US008309129B2

(12) United States Patent
Miller et al.

(10) Patent No.: US 8,309,129 B2
(45) Date of Patent: Nov. 13, 2012

(54) NANOPARTICLES COMPRISING A DRUG, ETHYLCELLULOSE, AND A BILE SALT

(75) Inventors: Warren Kenyon Miller, Bend, OR (US); Michael Mark Morgen, Bend, OR (US); Daniel Tod Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 260 days.

(21) Appl. No.: 12/451,287

(22) PCT Filed: Apr. 21, 2008

(86) PCT No.: PCT/IB2008/001059
§ 371 (c)(1),
(2), (4) Date: Nov. 3, 2009

(87) PCT Pub. No.: WO2008/135828
PCT Pub. Date: Nov. 13, 2008

(65) Prior Publication Data
US 2010/0119603 A1    May 13, 2010

Related U.S. Application Data

(60) Provisional application No. 60/915,696, filed on May 3, 2007.

(51) Int. Cl.
A61K 9/14 (2006.01)
A01N 43/42 (2006.01)
A01N 43/76 (2006.01)
A01N 43/56 (2006.01)
A01N 47/10 (2006.01)
A61K 31/47 (2006.01)
A61K 31/42 (2006.01)
A61K 31/415 (2006.01)
A61K 31/27 (2006.01)

(52) U.S. Cl. ........ 424/484; 424/489; 514/313; 514/378; 514/406; 514/487

(58) Field of Classification Search .................. 424/484
See application file for complete search history.

(56) References Cited

U.S. PATENT DOCUMENTS

| | | | |
|---|---|---|---|
| 3,960,757 A | 6/1976 | Morishita et al. |
| 4,107,288 A | 8/1978 | Oppenheim et al. |
| 4,158,707 A | 6/1979 | Steffen |
| 4,229,360 A | 10/1980 | Schneider |
| 4,298,594 A | 11/1981 | Sears |
| 4,329,332 A | 5/1982 | Couvreur et al. |
| 4,331,654 A | 5/1982 | Morris |
| 4,501,726 A | 2/1985 | Schroder |
| 4,610,868 A | 9/1986 | Fountain et al. |
| 4,615,881 A | 10/1986 | Deibig et al. |
| 4,639,370 A | 1/1987 | Carli |
| 4,649,155 A | 3/1987 | Steffen |
| 4,725,442 A | 2/1988 | Haynes |
| 4,728,513 A | 3/1988 | Ventouras |
| 4,731,210 A | 3/1988 | Weder et al. |
| 4,754,027 A | 6/1988 | Applegren |
| 4,826,689 A | 5/1989 | Violanto |
| 4,830,858 A | 5/1989 | Payne |
| 4,837,381 A | 6/1989 | Steber et al. |
| 4,880,634 A | 11/1989 | Speiser |
| 4,882,164 A | 11/1989 | Ferro et al. |
| 4,904,479 A | 2/1990 | Illum |
| 4,917,900 A | 4/1990 | Jones et al. |
| 4,997,454 A | 3/1991 | Violante |
| 5,049,322 A | 9/1991 | Devissaguet et al. |
| 5,051,261 A | 9/1991 | McGinity |
| 5,084,278 A | 1/1992 | Mehta |
| 5,085,864 A | 2/1992 | Cannon et al. |
| 5,091,187 A | 2/1992 | Haynes |
| 5,091,188 A | 2/1992 | Haynes |
| 5,112,621 A | 5/1992 | Stevens et al. |
| 5,118,528 A | 6/1992 | Fessi et al. |
| 5,133,908 A | 7/1992 | Stainmesse et al. |
| 5,145,684 A | 9/1992 | Liversidge et al. |
| 5,152,923 A | 10/1992 | Weder |
| 5,174,930 A | 12/1992 | Stainmesse et al. |
| 5,188,837 A | 2/1993 | Domb |
| 5,202,159 A | 4/1993 | Chen et al. |
| 5,298,262 A | 3/1994 | Na |
| 5,302,401 A | 4/1994 | Liversidge et al. |
| 5,314,506 A | 5/1994 | Midler et al. |
| 5,336,507 A | 8/1994 | Na |
| 5,340,591 A | 8/1994 | Nakano et al. |
| 5,352,459 A | 10/1994 | Hollister et al. |

(Continued)

FOREIGN PATENT DOCUMENTS

| | | |
|---|---|---|
| EP | 877033 A1 | 11/1998 |
| EP | 1180062 B1 | 3/2004 |
| EP | 710261 B1 | 5/2004 |
| WO | WO 9710811 A1 | 3/1997 |
| WO | WO 9713503 A1 | 4/1997 |
| WO | WO 9933558 A1 | 7/1999 |
| WO | WO02/11803 A1 * | 2/2002 |

OTHER PUBLICATIONS

Mithani, Sabena D, et al. "Estimation of the Increase in Solubility of Drugs as a Function of Bile Salt Concentration", Pharmaceutical Research, vol. 13, No. 1. Published Jan. 1996.*

Bodmeier R et al, "Indomethacin Polymeric Nanosuspensions Prepared by Microfluidization," Journal of Controlled Release, vol. 12, No. 3, May 1, 1990, pp. 223-233.

Al-Kassas, R., "Design and In Vitro Evaluation of Gentamicin-Eudragit Microspheres Intended for Intra-Ocular Administration," Journal of Microencapsulation, 21:1(2004)71-81.

Amrite, A.C., S.P. Ayalasomayajula, and U. Kompella, "Ocular Distribution of Intact Nano- and Micro Particles Following Subconjunctival and Systemic Routes of Administration," Drug Delivery Techn., vol. 2, No. 3, 2003.

(Continued)

Primary Examiner — Fereydoun G Sajjadi
Assistant Examiner — Audrea Buckley
(74) Attorney, Agent, or Firm — Chernoff, Vilhauer, McClung & Stenzel LLP

(57) ABSTRACT

A pharmaceutical composition comprises nanoparticles comprising a poorly water-soluble drug, ethylcellulose, and a bile salt.

19 Claims, 1 Drawing Sheet

U.S. PATENT DOCUMENTS

| | | |
|---|---|---|
| 5,370,880 A | 12/1994 | Jones et al. |
| 5,445,830 A | 8/1995 | Ishizue et al. |
| 5,456,923 A | 10/1995 | Nakamichi et al. |
| 5,470,583 A | 11/1995 | Na |
| 5,484,608 A | 1/1996 | Rudnic et al. |
| 5,494,683 A | 2/1996 | Liversidge et al. |
| 5,510,118 A | 4/1996 | Bosch et al. |
| 5,534,270 A | 7/1996 | De Castro |
| 5,543,158 A | 8/1996 | Gref et al. |
| 5,552,160 A | 9/1996 | Liversidge et al. |
| 5,556,642 A | 9/1996 | Kobayashi et al. |
| 5,560,931 A | 10/1996 | Eickhoff et al. |
| 5,560,932 A | 10/1996 | Bagchi et al. |
| 5,565,188 A | 10/1996 | Wong et al. |
| 5,565,215 A | 10/1996 | Gref et al. |
| 5,569,448 A | 10/1996 | Wong et al. |
| 5,569,469 A | 10/1996 | Lovrecich |
| 5,571,536 A | 11/1996 | Eickhoff et al. |
| 5,573,783 A | 11/1996 | Desieno |
| 5,576,016 A | 11/1996 | Amselem |
| 5,578,325 A | 11/1996 | Domb et al. |
| 5,585,108 A | 12/1996 | Ruddy et al. |
| 5,622,938 A | 4/1997 | Wong |
| 5,662,883 A | 9/1997 | Bagchi et al. |
| 5,662,932 A | 9/1997 | Amselem |
| 5,665,277 A | 9/1997 | Johnson et al. |
| 5,665,331 A | 9/1997 | Bagchi et al. |
| 5,667,800 A | 9/1997 | De Vringer |
| 5,679,690 A | 10/1997 | Andre et al. |
| 5,683,723 A | 11/1997 | Spenlehauer et al. |
| 5,705,196 A | 1/1998 | Galan Valdivia et al. |
| 5,707,634 A | 1/1998 | Schmitt |
| 5,716,642 A | 2/1998 | Bagchi et al. |
| 5,718,919 A | 2/1998 | Ruddy et al. |
| 5,780,062 A | 7/1998 | Frank et al. |
| 5,783,211 A | 7/1998 | Manzo et al. |
| 5,785,976 A | 7/1998 | Westesen |
| 5,834,025 A | 11/1998 | de Garavilla et al. |
| 5,843,509 A | 12/1998 | Calvo Salve et al. |
| 5,853,753 A | 12/1998 | Maierhofer et al. |
| 5,874,111 A | 2/1999 | Maitra et al. |
| 5,885,486 A | 3/1999 | Westesen et al. |
| 5,889,051 A | 3/1999 | Chen et al. |
| 5,919,408 A | 7/1999 | Muller et al. |
| 5,932,249 A | 8/1999 | Gruber et al. |
| 5,935,939 A | 8/1999 | Kararli et al. |
| 5,952,005 A | 9/1999 | Olsson et al. |
| 5,968,551 A | 10/1999 | Oshlack |
| 6,007,845 A | 12/1999 | Domb et al. |
| 6,020,004 A | 2/2000 | Shah |
| 6,027,747 A | 2/2000 | Terracol |
| 6,083,529 A | 7/2000 | Manzo et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee |
| 6,177,103 B1 | 1/2001 | Pace et al. |
| 6,197,348 B1 | 3/2001 | Morella et al. |
| 6,197,349 B1 | 3/2001 | Westesen |
| 6,207,178 B1 | 3/2001 | Westesen |
| 6,217,901 B1 | 4/2001 | Perrott |
| 6,235,224 B1 | 5/2001 | Mathiowitz et al. |
| 6,245,349 B1 | 6/2001 | Yiv et al. |
| 6,254,889 B1 | 7/2001 | Kigoshi et al. |
| 6,267,985 B1 | 7/2001 | Chen et al. |
| 6,267,989 B1 | 7/2001 | Liversidge et al. |
| 6,268,053 B1 | 7/2001 | Woiszwillo et al. |
| 6,270,806 B1 | 8/2001 | Liversidge |
| 6,280,770 B1 | 8/2001 | Pather et al. |
| 6,303,560 B1 | 10/2001 | Hartan et al. |
| 6,361,944 B1 | 3/2002 | Mirkin et al. |
| 6,375,986 B1 | 4/2002 | Ryde |
| 6,383,500 B1 | 5/2002 | Wooley et al. |
| 6,391,338 B1 | 5/2002 | Frisbee et al. |
| 6,406,745 B1 | 6/2002 | Talton |
| 6,428,814 B1 | 8/2002 | Bosch et al. |
| 6,440,458 B1 | 8/2002 | Yamashita et al. |
| 6,443,898 B1 | 9/2002 | Unger et al. |
| 6,447,806 B1 | 9/2002 | Gassmann |
| 6,458,383 B2 | 10/2002 | Chen et al. |
| 6,462,093 B1 | 10/2002 | Miyamoto |
| 6,479,146 B1 | 11/2002 | Caruso et al. |
| 6,485,743 B1 | 11/2002 | Jung et al. |
| 6,509,034 B1 | 1/2003 | Calanchi et al. |
| 6,517,859 B1 | 2/2003 | Tice et al. |
| 6,537,579 B1 | 3/2003 | Desai et al. |
| 6,544,497 B2 | 4/2003 | Zhu et al. |
| 6,548,264 B1 | 4/2003 | Tan et al. |
| 6,551,619 B1 | 4/2003 | Penkler et al. |
| 6,555,139 B2 | 4/2003 | Sharma |
| 6,565,873 B1 | 5/2003 | Shefer |
| 6,565,875 B2 | 5/2003 | Tice et al. |
| 6,565,885 B1 | 5/2003 | Tarara et al. |
| 6,576,264 B1 | 6/2003 | Henriksen et al. |
| 6,579,519 B2 | 6/2003 | Maitra et al. |
| 6,592,899 B2 | 7/2003 | Fowers et al. |
| 6,592,901 B2 | 7/2003 | Durig et al. |
| 6,592,903 B2 | 7/2003 | Ryde |
| 6,596,262 B2 | 7/2003 | Zhu et al. |
| 6,596,311 B1 | 7/2003 | Dobetti |
| 6,607,784 B2 | 8/2003 | Kipp et al. |
| 6,616,869 B2 | 9/2003 | Mathiowitz et al. |
| 6,620,351 B2 | 9/2003 | Gupta |
| 6,623,761 B2 | 9/2003 | Hassan |
| 6,632,671 B2 | 10/2003 | Unger |
| 6,638,537 B2 | 10/2003 | Dennis et al. |
| 6,638,621 B2 | 10/2003 | Anderson |
| 6,638,994 B2 | 10/2003 | Crooks et al. |
| 6,645,517 B2 | 11/2003 | West et al. |
| 6,645,569 B2 | 11/2003 | Cramer et al. |
| 6,649,192 B2 | 11/2003 | Alonso Fernandez et al. |
| 6,652,967 B2 | 11/2003 | Yadav et al. |
| 6,656,504 B1 | 12/2003 | Bosch et al. |
| 6,656,507 B2 | 12/2003 | Petereit et al. |
| 6,656,984 B1 | 12/2003 | Haasmaa et al. |
| 6,660,382 B2 | 12/2003 | Nouri et al. |
| 6,663,885 B1 | 12/2003 | Hager et al. |
| 6,669,959 B1 | 12/2003 | Adjei et al. |
| 6,677,386 B1 | 1/2004 | Giezen et al. |
| 6,682,761 B2 | 1/2004 | Pace |
| 6,682,895 B2 | 1/2004 | Mirkin et al. |
| 6,685,960 B1 | 2/2004 | Gasco |
| 6,692,769 B1 | 2/2004 | Ishibashi et al. |
| 6,696,084 B2 | 2/2004 | Pace et al. |
| 6,696,090 B1 | 2/2004 | Nilsson et al. |
| 6,709,622 B2 | 3/2004 | Billiet |
| 6,720,008 B2 | 4/2004 | Allison |
| 6,726,934 B1 | 4/2004 | Prokop |
| 6,746,635 B2 | 6/2004 | Mathiowitz et al. |
| 6,755,915 B1 | 6/2004 | Van Soest et al. |
| 6,756,062 B2 | 6/2004 | Johnston et al. |
| 6,761,903 B2 | 7/2004 | Chen et al. |
| 6,780,324 B2 | 8/2004 | Le Garrec et al. |
| 6,793,938 B2 | 9/2004 | Sankaram |
| 6,824,791 B2 | 11/2004 | Mathiowitz et al. |
| 6,827,946 B2 | 12/2004 | Hirsh |
| 6,863,914 B1 | 3/2005 | Auweter et al. |
| 6,869,617 B2 | 3/2005 | Kipp et al. |
| 6,878,693 B2 | 4/2005 | Goldshtein |
| 6,887,493 B2 | 5/2005 | Shefer |
| 6,890,512 B2 | 5/2005 | Roser et al. |
| 7,081,450 B2 | 7/2006 | Goldshtein |
| 7,105,176 B2 | 9/2006 | Auweter et al. |
| 2002/0012675 A1 | 1/2002 | Jain et al. |
| 2002/0054914 A1 | 5/2002 | Morcol |
| 2002/0068092 A1 | 6/2002 | Bosch et al. |
| 2002/0081334 A1 | 6/2002 | Johnston et al. |
| 2002/0106403 A1 | 8/2002 | Parikh et al. |
| 2002/0127278 A1 | 9/2002 | Kipp et al. |
| 2002/0142017 A1 | 10/2002 | Simonnet |
| 2003/0003155 A1 | 1/2003 | Kipp et al. |
| 2003/0026844 A1 | 2/2003 | Lee et al. |
| 2003/0031719 A1 | 2/2003 | Kipp et al. |
| 2003/0049323 A1 | 3/2003 | Hitt et al. |
| 2003/0072801 A1* | 4/2003 | Curatolo et al. ............. 424/465 |
| 2003/0095928 A1 | 5/2003 | McGurk et al. |
| 2003/0129239 A1 | 7/2003 | Goldshtein |

| | | | |
|---|---|---|---|
| 2003/0147965 A1 | 8/2003 | Bassett et al. | |
| 2003/0166509 A1 | 9/2003 | Edwards et al. | |
| 2003/0170309 A1 | 9/2003 | Babcock et al. | |
| 2003/0190347 A1 | 10/2003 | Supersaxo et al. | |
| 2003/0206949 A1 | 11/2003 | Parikh et al. | |
| 2003/0235619 A1 | 12/2003 | Allen et al. | |
| 2004/0009229 A1 | 1/2004 | Unger et al. | |
| 2004/0013613 A1 | 1/2004 | Jain et al. | |
| 2004/0018229 A1 | 1/2004 | Henriksen et al. | |
| 2004/0018236 A1 | 1/2004 | Gurny et al. | |
| 2004/0047913 A1 | 3/2004 | Allemann et al. | |
| 2004/0067251 A1 | 4/2004 | Johnston et al. | |
| 2004/0071776 A1 | 4/2004 | Boudy et al. | |
| 2004/0091546 A1 | 5/2004 | Johnson | |
| 2004/0180005 A1 | 9/2004 | Jurgens | |
| 2004/0191319 A1 | 9/2004 | Yun | |
| 2004/0220081 A1 | 11/2004 | Kreitz et al. | |
| 2004/0245662 A1 | 12/2004 | Chaubal et al. | |
| 2004/0247624 A1 | 12/2004 | Unger et al. | |
| 2005/0013866 A1 | 1/2005 | Maincent et al. | |
| 2005/0238716 A1 | 10/2005 | Verrijk et al. | |
| 2006/0134220 A1 | 6/2006 | Aboubakar et al. | |

OTHER PUBLICATIONS

Barbu, E., L. Verestiuc, T.G. Nevell, and J. Tsibouldis, "Polymeric Materials for Ophthalmic Drug Delivery: Trends and Perspectives," J. of Materials Chemistry, 16(2006)3439-3443.

Bodmeier et al., "Preparation and Evaluation of Drug-Containing Polymeric Nanosuspensions," presented at the 5th International Conference on Pharmaceutical Technology, Paris, France, 1989. Proceedings vol. 2, pp. 265-268.

Bodmeier, et al., "Indomethacin Polymer Nanosuspension Prepared by Microfluidization", Journal of Controlled Release, 12 (1990) 223-233.

Bourges, J.-L., S.E. Gautier, F. Delie, R.A. Bejjani, J.-C. Jeanny, R. Gurny, D. BenEzra, and F.F. Behar-Cohen, "Ocular Drug Delivery Targeting the Regina and Retinal Pigment Epithelium Using Polylactide Nanoparticles," Investigative Ophthalmology and Visual Science, 44:8(2003)3562-3569.

Briancon, S., H. fessi, F. Lecomet, and J. Lieto, "Study and Scale-Up of a Nanoprecipitation Process," Industrial Crystallization 1999 (IChemE), pp. 1-10.

Bucolo, C., A. Maltese, F. Maugeri, B. Busa, G. Puglisi, and R. Pignatello, "Eudragit RL100 Nanoparticle System for the Ophthalmic Delivery of Cloricromene," Journal of Pharmacy and Pharmacology, 56(2004)841 846.

Calvo, P., J.L. Vila-Jato, and M.J. Alonso, "Evaluation of Cationic Polymer-Coated Nanocapsules as Ocular Drug Carriers," International Journal of Pharmaceutics, 153(1997)41-50.

Carrasquillo, K.G., J.A. Ricker, I.K. Rigas, J.W. Miller, E.S. Gragoudas, and A.P. Adamis, "Controlled Delivery of the Anti-VEGF Aptamer EYE001 with Poly(lactic-co-glycolic) Acid Microspheres," Investigative Ophthalmology and Visual Science, 44:1(2003)290-299.

Cavalli, R., M.R. Gasco, P. Chetoni, S. Burgalassi, and M.F. Saettone, "Solid Lipid Nanoparticles (SLN) as Ocular Delivery System for Tobramycin," International J. Pharmaceutics, 238(2002)241-245.

Chen et al., "Comparison of Albumin and Casein Microspheres as a Carrier for Doxorubicin," J. Pharm. Pharmacol.39(1987)978-985.

Chiou, W.L., and S.Riegelman, J. Pharm. Sci., 60:9(1971)1281-1302.

Couvreur, Microspheres and Drug Therapy, Elsevier, (1984) pp. 103-115.

De, T.K., D.J. Rodman, B.A. Holm, P.N. Prasad, and E.J. Bergey, "Brimonidine Formulation in Polyacrylic Acid Nanoparticles for Ophthalmic Delivery," J. Microencapsualtion, 20:3)2003)361-374.

Decampos, A.M., A. Sanchez, and M.J. Alonso, "Chitosan Nanoparticles: A New Vehicle for the Improvement of the Delivery of Drugs to the Ocular Surface. Application to Cyclosporin A," International J. of Pharmaceutics, 224(2001)159-168.

Decampos., A.M., A. Sanchez, R. Gref, P. Calvo, and M.J. Alonso, "The Effect of a PGE Versus a Chitosan Coating on the Interaction of Drug Colloidal Carriers with the Ocular Mucosa," European Journal of Pharmaceutical Sciences, 20(2003)73-81.

Dejaeghere, F., E. Allemann, J.-C. Leroux, W. Stevels, J. Feijen, E. Doelker, and R. Gurny, "Formulation of Lyoprotection of Poly(Lactic Acid-Co-Ethylene Oxide) Nanoparticles: Influence on Physical Stability and in Vitro cell Uptake," Pharmaceutical Research, 16:6(1999)859-866.

Desai, S.D., and J. Blanchard, "Pluronic F127-Based Ocular Delivery System Containing Biodegradable Polyisobutylcyanoacrylate Nanocapsules of Pilocarpine," Drug Delivery, 7(2000)201-207.

Fee, C.A., and R.I. Pettigrew, "National Institute of Biomedical Imaging and Bioengineering: Poised for the Future," National Institute of Biomedical Imaging and Bioengineering, 229:3(2003)636-637.

Fessi, H., F. Puisieux, J.Ph. Devissaguet, N. Ammoury, and S. Benita, "Nanocapsule Formation by Interfacial Polymer Deposition Following Solvent Displacement," International J. of Pharmaceutics, 55(1989)R1-R4.

Ford, J.L., Pharm. Acta Helv., 61:3(1986)69-87.

Fox et al., from Proteins in Food Processing, R.Y. Yada (ed), CRC Press, 2004, Chapter 3: The Caseins pp. 29-71.

Gavini, E., P. Chetoni, M. Cossu, M.G. Alvarez, M.F. Saettone, and P. Giunchedi, "PLGA Microspheres for the Ocular Delivery of a Peptide Drug, Vancomycin Using Emulsification/Spray-Drying as the Preparation Method: In Vitro/In Vivo Studies," European Journal of Pharmaceutics and Biopharmaceutics, 57(2004)207-212.

Giannavola, C., C. Bucolo, A. Maltese, D. Paolino, M.A. Vandelli, G. Puglisi, V.H.L. Lee, and M. Fresta, "Influence of Preparation Conditions on Acyclovir-Loaded Poly-d,l-Lactic Acid Nanospheres and Effect of PEG Coating on Ocular Drug Bioavailability." Pharmaceutical Research, 20:4(2003)584-590.

Gurny, Drug Develop. Ind. Pharm. 7(1), 1-25, 1981.

Gurny, R., T. Boye, and H. Ibrahim, "Ocular Therapy with Nanoparticulate Systems for Controlled Drug Delivery," Journal of Controlled Release, 2(1985)353-361.

Harmia, J. Microencapsulation, 1986 vol. 3, No. 1, p. 3-12.

Hasegawa, H., et al., Chem. Pharm. Bull., 33:4(1985)1615-1619; Chem. Pharm. Bull., 34:5(1986)2183-2190; Chem. Pharm. Bull., 36:12(1988) 4941-4950.

Herrero-Vanrell, R., and M.F. Refojo, "Biodegradable Microspheres for Vitreoretinal Drug Delivery," Advanced Drug Delivery Reviews, 52(2001)5 16.

Hornig et al., "Novel Nanoparticles Based on Dextran Esters with Unsaturated Moieties," Macromolecular Rapid Commun., 2005, 26, 1908-1912.

Hornig et al., "Structure Design of Multifunctional Furoate and Pyroglutamate Esters of Dextran by Polymer-Analogous Reactions," Macromol. Biosci. 2007, 7, 297-306.

Hsiue, G.-H., S.-H. Hsu, C.-C. Yang, S.-H. Lee,a nd I.-K. Yang, "Preparation of Controlled Release Ophthalmic Drops, for Glaucoma Therapy Using Thermosensitive poly-N-Isopropylacrylamide," Biomaterials, 23(2002)457 462.

Kim, S., Y.T. Lim, E.G. Soltesz, A.M. DeGrand, J. Lee, A. Nakayama, J.A. Parker, T. Mihaljevic, R.G. Laurence, D.M. Dor, L.H. Cohn, M.G. Bawendi, and J.V. Frangioni, "Near-Infrared Fluorescent Type II Quantum Dots for Sentinel Lymph Node Mapping," Nature Biotechnology, 22:1(2004)93-97.

Knepp et al., Synthesis, Properties, and Intratumoral Evaluation of Mitoxantrone-Loaded Casein Microspheres in Lewis Lung Carcinoma, J. Pharm. Pharmacol., 45(1993)887-891.

Kompella, U.B., N. Bandi, and S.P. Ayalasomayajula, "Subconjunctival Nano- and Microparticles Sustain Retinal Delivery of Budesonide, A Corticosteroid Capable of Inhibiting VEGF Expression," Investigative Ophthalmology and Visual Science, 44:3(2003)1192-1201.

Kumar, M.N.V., "Nano and Microparticles as Controlled Drug Delivery devices," J. Pharm. Pharmaceutical Sciences, 3:2(2000)234-258.

Latha et al., Casein as a Carrier Matrix for 5-Fluorouracil: Drug Release from Microspheres, Drug-Protein Conjugates and In-Vivo Degradation of Microspheres in Rat Muscle, J. Pharm. Pharmacol., 46(1994)858-862.

Latha et al., Glutaraldehyde Cross-Linked Bovine Casein Microspheres as a Matrix for the Controlled Release of Theophylline: In Vitro Studies, J. Pharm. Pharmacol., 46(1994)8-13.

Latha et al., Progesterone Release from Glutaraldehyde Cross-Linked Casein Microspheres: In Vitro Studies and In Vivo Response in Rabbits, Contraception, 61(2000)329-334.

Lecorre, P., J.H. Rytting, V. Gajan, F. Chevanne, and R. LeVerge, "In Vitro Controlled Release Kinetics of Local Anaesthetics from Poly(D,L-lactice) and Poly (lactice-co-glycolide) Microspheres," Journal of Microencapsulation, 1997, pp. 243-255.

Lellemand, F., O. Felt-Baeyens, K. Besseghir, F. Behar-Cohen, and R. Gurny, "Cyclosporine A Delivery to the Eye: A Pharmaceutical Challenge," European J. of Pharmaceutics and Biopharmaceutics, 56(2003)307 318.

Lemarchand, C., R. Gref, and P. Couvreur, "Polysaccharide-Decorated Nanoparticles," European J. of Pharmaceutics and Biopharmaceutics, 58(204,327-341.

Lemarchand, et al., "Influence of polysaccharide coating on the interactions of nanoparticles with biological systems," Biomaterials, 27(2006)108-118.

Liebert, et al., "Nanoparticles on the Basis of Highly Functionalized Dextrans," J. Am. Chem. Soc. 2005, 127, 10484-10485.

Longmuir, K.J., R.T. Robertson, S.M. Haynes, J.L. Baratta, and A.J. Waring, "Effective Targeting of Liposomes to Liver and Hepatocytes In Vivo by Incorporation of a Plasmodium Amino Acid Sequence," Pharmaceutical Research, 23:4(2006)759-769.

Losa, C., L. Marchal-Heussler, F. Orallo, J.L. Vila Jato, and M.J. Alonso, "Design of New Formulations for Topical Ocular Administration: Polymeric Nanocapsules Containing Metipranolol," Pharmaceutical Research, 10:1(1993)80-87.

Merodio, M., J.M. Irache, F. Valamanesch, and M. Mirshahi, "Ocular Disposition and Tolerance of Ganciclovir-Loaded Albumin Nanoparticles after Intravitreal Injection in Rats," Biomaterials, 23(2002)1587-1594.

Mirshahi et al., Development of Drug Delivery Systems from Vegetal Proteins: Legumin Nanoparticles, Drug Dev. Indust.Pharm., 22:8(1996)841-846.

Mora-Gutierrez et al., Modeling Calcium-Induced Solubility in Caprine Milk Caseins Using a Thermodynamic Linkage Approach, J. Dairy Sci., 76(1993)3698-3710.

Ohio State FST 822 Class Lecture, Casein, 2006, 5 pp.

Pignatello, R., C. Bucolo, and G. Puglisi, "Ocular Tolerability of Eudragit RS100 and RL100 Nanosuspensions as Carriers for Ophthalmic Controlled Drug Delivery," Journal of Pharmaceutical Sciences, 91:12(2002)2636-2641.

Pignatello, R., C. Bucolo, G. Spedalieri, A. Maltese, and G. Puglisi, "Flurbiprofen-Loaded Acrylate Polymer Nanosuspensions for Ophthalmic Application," Biomaterials, 23(2002)3247-3255.

Pignatello, R., C. Bucolo, P. Ferra, A. Maltese, A. Puleo, and G. Puglisi, "Eudragit RS100 Nanosuspensions for the Ophthalmic Controlled Delivery of Ibuprofen," European Journal of Pharmaceutical Sciences, 16(2002)53 61.

Qaddoumi, M.G., H. Ueda, J. Yang, J. Davda, V. Labhasetwar, and V.H.L. Lee, "The Characteristics and Mechanisms of Uptake of PLGA Nanoparticles in Rabbit Conjuctival Epithelial Cell Layers," Pharmaceutical Research, 21:4(2004)641-648.

Raveendran, P., J. Fu, and S.L. Wallen, "Completely 'Green' Synthesis and Stabilization of Metal Nanoparticles," J. American Chemical Society, 125(2003)13940-13941.

Santinho et al., Influence of Formulation on the Physiochemical Properties of Casein Microparticles, Int'l J. Pharm., 186(1999)191-198.

Scholes, P.D., A.G.A. Coombes, L. Illum, S.S. Savis, M. Vert, and M.C. Davies, "The Preparation of Sub-200 nm Poly(lactide-co-glycolide) Microspheres for Site-Specific Drug Delivery," J. Controlled Release, 25(1993)145-153.

Sjostrom, et al., Journal of Pharmaceutical Sciences, vol. 82, No. 6 Jun. 1993, pp. 584-589.

Sugimoto, I., K. Sasaki, A. Kuchiki, T. Ishihara, and H. Nakagawa, Chem. Pharm. Bull, 30:12(1982)4479-4488.

Suverkrup, R., S. Grunthal, O. Krasichkova, S. Maier, A. Weischselbaum, B. Neff, M. Diestelhorst, S. Dinslage, and A. Lux, "The Ophthalmic Lyophilisate Carrier System (OLCS): Development of a Novel Dosage Form, Freeze-Drying Technique, and In Vitro Quality Control Tests," European J. Pharmaceutics and Biopharmaceutics, 57(2004)269-277.

Takayama, K., N. Nambu, and T. Nagai., Chem. Pharm. Bull., 30:2(1982)673-678.

Takenaka, H., Y. Kawashima and S.Y. Lin, J. Pharm. Sci., 69:12(1980)1388-1392.

Takeuchi, H., T. Handa and Y. Kawashima, Chem. Pharm. Bull., 35:9(1987)3800-3806.

Tuovinen, L., E. Ruhanen, T. Kinnarinen, S. Ronkko, J. Pelkonen, A. Urtti, S. Peltonen, and K. Jarvinen, "Starch Acetate Microparticles for Drug Delivery Into Retinal Pigment Epithelium—In Vitro Study," J. of Controlled Release, 98(2004)407-413.

Ueda, M., A. Iwara, and J. Kreuter, "Influence of the Preparation Methods on the Drug Release Behaviour of Loperamide-Loaded Nanoparticles," J. Microencapsulation, 15:3(1998)361-372.

University of Guelph, Dairy Chemistry and Physics, 2006, 16 pp.

Vandamme, Th.F., "Microemulsions as Ocular Drug Delivery Systems: Recent Developments and Future Challenges," Progress in Retinal and Eye Research, 21(2002)15-34.

Vandervoort, J., and A. Ludwig, "Preparation and Evaluation of Drug-Loaded Gelatin Nanoparticles for Topical Ophthalmic Use," European J. of Pharmaceutics and Biopharmaceutics, 57(2004)251-261.

Willmott et al., Doxorubicin-Loaded Casein Microspheres: Protean Nature of Drug Incorporation J. Pharm. Pharmacol. 42(1992)472-475.

Zahr, A.S., M. de Villiers, and M.V. Pishko, "Encapsulation of Drug Nanoparticles in Self-Assembled Macromolecular Nanoshells," Langmuir, 21(2005)503 410.

Zimmer, A., and J. Kreuter, "Microspheres and Nanoparticles Used in Ocular Delivery Systems," Advanced Drug Delivery Reviews, 16(1995)61-73.

\* cited by examiner

NANOPARTICLES COMPRISING A DRUG, ETHYLCELLULOSE, AND A BILE SALT

This is a 371 of PCT/IB2008/001059 filed 21 Apr. 2008, and claims priority of U.S. 60/915,696 filed 3 May 2007.

BACKGROUND OF THE INVENTION

The present invention relates to nanoparticles comprising a poorly water-soluble drug, ethylcellulose, and a bile salt.

It is known that poorly water-soluble drugs may be formulated as nanoparticles. Nanoparticles are of interest for a variety of reasons, such as to improve the bioavailability of poorly water-soluble drugs, to provide targeted drug delivery to specific areas of the body, to reduce side effects, or to reduce variability in vivo.

A variety of approaches have been taken to formulate drugs as nanoparticles. One approach is to decrease the size of crystalline drug by grinding or milling the drug in the presence of a surface modifier. See, e.g., U.S. Pat. No. 5,145,684. Another approach to forming nanoparticles is to precipitate the drug in the presence of a film forming material such as a polymer. See, e.g., U.S. Pat. No. 5,118,528.

Nanoparticles containing a drug and ethylcellulose are known in the art. See, for example, U.S. Pat. Nos. 5,919,408, 5,118,528, EP 1 180 062 B1, and Bodmeier and Chen (*J. Controlled Release*, 12, (1990) 223-233). The prior art nanoparticle formulations often included a surfactant to stabilize the nanoparticles.

While these formulations may be functional, nevertheless there remain a number of problems associated with the use of nanoparticles to deliver pharmaceutical compounds to the body. The nanoparticles must be stabilized so that they do not aggregate into larger particles. Often surface modifiers such as surfactants are used to stabilize the nanoparticles, but such materials can have adverse physiological effects when administered in vivo. In addition, without a surface modifier present, the surface of the nanoparticles is unprotected, leading to a decrease in performance and stability. Additionally, when formulated as a dry material, the composition should spontaneously form nanoparticles when the composition is added to an aqueous use environment.

Accordingly, there is still a continuing need for nanoparticles that are stable, in the sense of not forming crystalline drug over time or aggregating into larger particles, and that improve the bioavailability of low-solubility drugs.

BRIEF SUMMARY OF THE INVENTION

In a first aspect, a pharmaceutical composition comprises nanoparticles, the nanoparticles comprising: (a) a poorly water soluble drug having a solubility in water of less than 5 mg/mL over the pH range of 6.5 to 7.5 at 25° C., at least 90 wt % of the drug in the nanoparticles being non-crystalline; (b) ethylcellulose; and (c) a bile salt; wherein (i) the nanoparticles have an average size of less than 500 nm; (ii) the drug constitutes from 0.1 wt % to 75 wt %, the ethylcellulose constitutes from 2 wt % to 85 wt %, and the bile salt constitutes from 0.5 wt % to 60 wt % of the total mass of the drug, ethylcellulose, and bile salt in the nanoparticles; and (iii) the drug, the ethylcellulose, and the bile salt collectively constitute at least 80 wt % of the nanoparticles.

Compositions comprising nanoparticles of a drug, ethylcellulose, and a bile salt provide a number of advantages over the prior art. Because two materials are used to form the drug-containing nanoparticles—ethylcellulose and a bile salt—the stability of the non-crystalline drug and the suspension stability of the nanoparticle can be addressed independently, resulting in nanoparticles with improved performance and stability.

First, the ethylcellulose helps stabilize the poorly water soluble drug. Ethylcellulose was chosen because many poorly water-soluble drugs are soluble in the polymer. Ethylcellulose also has a high glass-transition temperature (Tg). These factors help prevent or reduce the rate of crystallization of the non-crystalline drug in the nanoparticle. It is well known that the non-crystalline form of a low-solubility drug provides a greater aqueous concentration of drug relative to the crystalline form of the drug when administered to an aqueous use environment. However, it is also well known that when the drug is not stabilized in the non-crystalline form, the drug rapidly converts to the crystalline form in the use environment. See, for example, Hancock and Parks (*Pharmaceutical Research*, Vol. 17, No. 4, 2000). Thus, the ethylcellulose helps maintain the stability of the non-crystalline drug in the nanoparticle and while suspended in an aqueous solution, resulting in an enhanced concentration of free drug when the nanoparticle is administered to an aqueous use environment.

Second, the bile salt helps promote stability of nanoparticle suspensions, reducing, slowing, or preventing agglomeration of the nanoparticles.

Finally, the nanoparticles of the invention may provide improved toleration relative to conventional nanoparticles that incorporate a substantial amount of a surfactant to stabilize the nanoparticles. The nanoparticles of the present invention may be especially suitable for parenteral dosage forms—some bile salts are already used in approved intravenous (IV) formulations. Use of bile salts also allows for the formation of smaller nanoparticles than when using other stabilizers, such as surfactants.

The foregoing and other objectives, features, and advantages of the invention will be more readily understood upon consideration of the following detailed description of the invention.

DETAILED DESCRIPTION OF THE INVENTION

Figure 1:
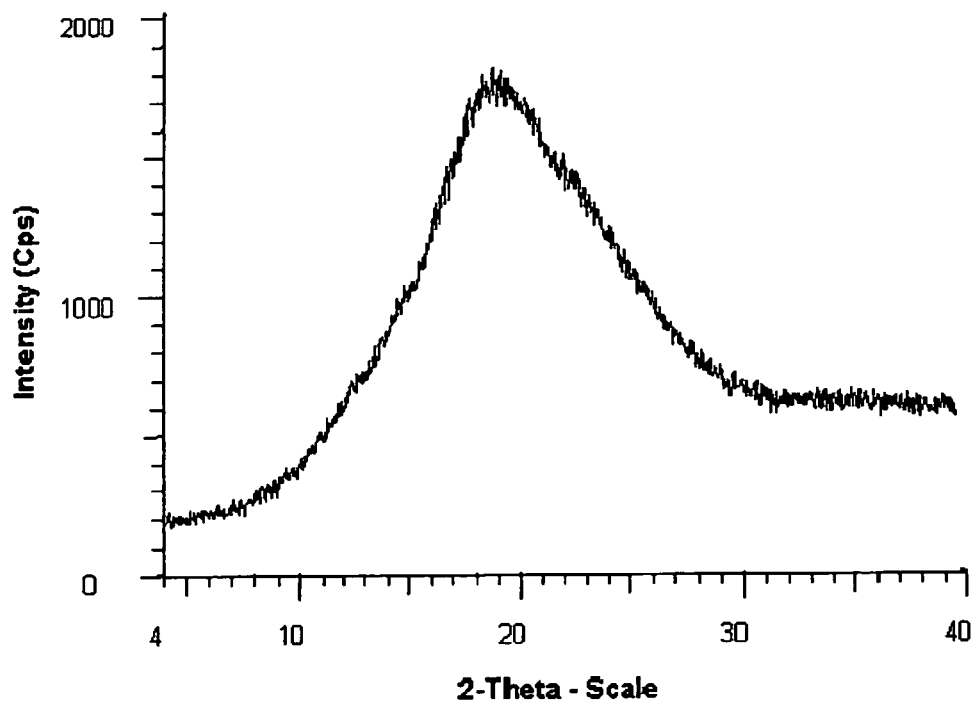
FIG. 1. is the Powder X Ray Diffraction (PXRD) diffraction pattern of the nanoparticles of Example 10.

The nanoparticles of the present invention comprise a poorly water soluble drug, ethylcellulose, and a bile salt. At least 90 wt % of the drug in the nanoparticle is non-crystalline. The nature of the nanoparticles, suitable drugs, and methods for making nanoparticles are described in detail below.

Nanoparticles

The nanoparticles are small particles comprising the drug, ethylcellulose, and a bile salt. By "nanoparticles" is meant a plurality of small particles in which the average size of the particles in suspension is less than about 500 nm. By "average size" is meant the effective cumulant diameter as measured by dynamic light scattering, using for example, Brookhaven Instruments' 90Plus particle sizing instrument. By "size" is meant the diameter for spherical particles, or the maximum diameter for non-spherical particles. Preferably, the average size of the nanoparticles is less than 400 nm, more preferably less 300 nm, more preferably less than 150 nm, more preferably less than 100 nm, and most preferably less than 75 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," *Applied Optics*, 40(24), 4087-4091 (2001) for a discussion of cumulant diameter and polydispersity. Preferably, the polydispersity of the nanoparticles is less than 0.5. More preferably, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 150 nm with a polydispersity of 0.5 or less. In yet another embodiment, the average size of the nanoparticles is less than 150 nm with a polydispersity of 0.3 or less.

At least 90 wt % of the drug in the nanoparticles is non-crystalline. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. As previously discussed, the non-crystalline form of a low-solubility drug is preferred as it provides a greater aqueous concentration of drug relative to the crystalline form of the drug in an aqueous use environment. Preferably at least about 95 wt % of the drug in the nanoparticle is non-crystalline; in other words, the amount of drug in crystalline form does not exceed about 5 wt %. Amounts of crystalline drug may be measured by Powder X-Ray Diffraction (PXRD), by Differential Scanning Calorimetry (DSC), by solid state nuclear magnetic resonance (NMR), or by any other known quantitative measurement.

The nanoparticles can exist in a number of different configurations. In one embodiment, the nanoparticles comprise a core, the core comprising the non-crystalline drug and ethylcellulose. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, fourier transform infra red (FTIR) analysis, and raman spectroscopy; (3) chromatographic techniques, such as high performance liquid chromatography (HPLC), and gel-permeation chromatography (GPC); and (4) other techniques known in the art.

In one embodiment, the non-crystalline drug and ethylcellulose constitute at least 60 wt % of the core, more preferably at least 80 wt % of the core. In another embodiment, the core consists essentially of the non-crystalline drug and ethylcellulose.

The non-crystalline drug present in the core can exist in non-crystalline pure drug domains, as a thermodynamically stable solid solution of non-crystalline drug homogeneously distributed throughout the ethylcellulose, as a supersaturated solid solution of non-crystalline drug homogeneously distributed throughout the ethylcellulose, or any combination of these states or those states that lie between them. When the glass-transition temperature ($T_g$) of the non-crystalline drug is different from the $T_g$ of ethylcellulose by at least about 20° C., the core may exhibit a $T_g$ that is different from the $T_g$ of pure non-crystalline drug or pure ethylcellulose. Preferably, less than 20 wt % of the drug is present in non-crystalline drug domains, with the remaining drug homogeneously distributed throughout the ethylcellulose.

In yet another embodiment, the core comprises the non-crystalline drug, the ethylcellulose, and a bile salt. The core may be (1) a homogeneous molecular mixture of drug, ethylcellulose, and bile salt, (2) domains of pure drug, domains of pure ethylcellulose, and domains of pure bile salt distributed throughout the core, or (3) any combination of these states or those states that lie between them. In one embodiment, the drug, ethylcellulose, and bile salt are homogeneously distributed throughout the core as a supersaturated solid solution. In another embodiment, the surface portion of the nanoparticle has a higher concentration of bile salt relative to the nanoparticle as a whole.

In still another embodiment, the core comprises the non-crystalline drug and ethylcellulose, with the bile salt adsorbed to the surface portion of the nanoparticle.

In yet another embodiment, the core comprises the non-crystalline drug, ethylcellulose, and a portion of the bile salt. The remaining portion of the bile salt is adsorbed to the surface portion of the nanoparticle. In this embodiment, a portion of the bile salt is integral to the core, while the remaining portion of bile salt is adsorbed to the surface portion of the nanoparticle.

The drug, ethylcellulose, and bile salt are collectively present in the nanoparticle in an amount ranging from about 80 wt % to 100 wt %. Preferably, the drug, ethylcellulose, and bile salt collectively constitute at least 85 wt %, more preferably at least 90 wt %, and even more preferably at least 95 wt % of the nanoparticle. In one embodiment, the nanoparticles consist essentially of the drug, ethylcellulose, and bile salt. By "consist essentially of" is meant that the nanoparticle contains less than 1 wt % of any other excipients and that any such excipients have no affect on the performance or properties of the nanoparticle.

The amount of drug in the nanoparticle can range from about 0.1 wt % drug to 75 wt % drug relative to the total mass of drug, ethylcellulose, and bile salt in the nanoparticle. Preferably, the amount of drug ranges from about 1 wt % to about 70 wt % drug, more preferably from about 2 wt % to about 65 wt %, and most preferably from about 5 wt % to about 60 wt % drug relative to the total mass of drug, ethylcellulose, and bile salt in the nanoparticle.

To minimize the total mass of the formulation, high drug loadings are desired. However, if the amount of drug in the nanoparticle is too high, the nanoparticle suspension becomes unstable, resulting in crystallization of the drug in the suspension. Additionally, high amounts of drug in the nanoparticle can lead to crystalline drug formation when the nanoparticles are isolated from suspension in solid form. In absolute terms, it is generally preferred that the amount of drug in the nanoparticle be less than about 75 wt %, and more preferably less than about 70 wt % the total mass of the drug, ethylcellulose, and bile salt in the nanoparticles.

The nanoparticles also comprise ethylcellulose. The ethyl content of the ethylcellulose may range from about 42 wt % to 51.5 wt % relative to the dried weight of the polymer, corresponding to an ethoxy degree of substitution ranging from 2 to about 3. "Degree of substitution" refers to the average number of the three hydroxyls per saccharide repeat unit on the cellulose chain that have been substituted with an ethyl group through an ether linkage. Preferably the degree of substitution of ethoxy groups ranges from about 2.2 to about 2.9. In one embodiment, the ethoxy degree of substitution ranges from about 2.3 to about 2.45. Examples of such polymers include the "Medium" grade of ETHOCEL® polymers available from Dow Chemical Co. (Midland, Mich.). In another embodiment, the ethoxy degree of substitution ranges from about 2.6 to about 2.8. Examples of such polymers include the "Standard" grade of ETHOCEL® polymers available from Dow Chemical Co.

The ethylcellulose can have a wide range of molecular weight. The molecular weight of the ethylcellulose is related to the viscosity of a solution of the ethylcellulose dissolved in a solvent, such as mixtures of toluene and ethanol. The viscosity of a 5 wt % solution of the ethylcellulose in a solvent of 80% toluene and 20% ethanol at 25° C. can range from about 2 cp to about 400 cp. Generally, for the nanoparticles of the present invention, ethylcellulose with a low molecular weight is preferred. In one embodiment, the viscosity of a 5 wt % solution of the ethylcellulose dissolved in a solvent of 80% toluene and 20% ethanol is about 110 cp or less, preferably about 70 cp or less, more preferably about 45 cp or less, even more preferably about 20 cp or less, and most preferably about 14 cp or less. Exemplary grades of ethylcellulose that are suitable for the nanoparticles of the present invention include ETHOCEL® Std. 4, ETHOCEL® Std. 7, ETHOCEL® Std. 10, ETHOCEL® Std. 14, ETHOCEL® Std. 20, ETHOCEL® Std. 45, ETHOCEL® Std. 100, ETHOCEL® Med. 50, and ETHOCEL® Med. 70, all of which are available from the Dow Chemical Co. In a preferred embodiment, the ethylcellulose is selected from the group consisting of ETHOCEL® Std. 4, ETHOCEL® Std. 7, and ETHOCEL® Std. 10.

The amount of ethylcellulose in the nanoparticle can vary over a wide range, depending on the properties of the drug. Generally, the amount of ethylcellulose in the nanoparticle will range from about 2 wt % to about 85 wt %, relative to the total mass of drug, ethylcellulose, and bile salt in the nanoparticle. Preferably, the concentration of ethylcellulose in the nanoparticle will range from about 5 wt % to about 80 wt %, even more preferably from about 10 wt % to 75 wt % relative to the total mass of drug, ethylcellulose, and bile salt in the nanoparticle.

The nanoparticles also comprise a bile salt. Bile salts are the alkaline salts of bile acids. The bile acids are divided into two groups: primary (derived from cholesterol) and secondary (derived from primary bile acids). The bile salts are conjugated through peptide linkages to glycine or taurine. The primary bile salts are taurine or glycine conjugates of cholic acid or chenic acid; the secondary bile salts are taurine and glycine conjugates of deoxycholic and lithocholic acids. See Remington the Science and Practice of Pharmacy (20$^{th}$ edition, 2000, at page 1228). The term "bile salt" includes mixtures of bile salts.

Exemplary bile salts include the salts of dihydroxy cholic acids, such as deoxycholic acid, glycodeoxycholic acid, taurodeoxycholic acid, chenodeoxycholic acid, glycochenodeoxycholic acid, and taurochenodeoxycholic acid, and trihydroxy cholic acids, such as cholic acid, glycocholic acid, and taurocholic acid. The alkaline salts include sodium, and potassium. Preferred bile salts include sodium glycocholate and sodium taurocholate.

The amount of bile salt in the nanoparticle can vary over a wide range depending on the properties of the drug and the relative amounts of drug and ethylcellulose in the nanoparticle. Generally, a sufficient amount of bile salt should be present in the nanoparticle to reduce or prevent agglomeration or flocculation of the nanoparticles. Generally, the amount of bile salt will range from about 0.5 wt % to about 60 wt %, relative to the total mass of drug, ethylcellulose, and bile salt in the nanoparticle. Preferably, the amount of bile salt will range from about 1 wt % to about 50 wt %, and more preferably, from about 5 wt % to about 45 wt % relative to the total mass of drug, ethylcellulose, and bile salt in the nanoparticle.

Preferred embodiments of nanoparticles have the following amount of drug, ethylcellulose, and bile salt, relative to the total amount of drug, ethylcellulose, and bile salt present in the nanoparticles:

0.1 wt % to 75 wt %, preferably 1 wt % to 60 wt % drug;
2 wt % to 85 wt %, preferably 5 wt % to 60 wt % ethylcellulose; and
0.5 wt % to 60 wt %, preferably 1 wt % to 50 wt % bile salt.

The nanoparticle is preferably substantially free from surfactants. By a "surfactant" is meant a surface-active material having a hydrophobic portion and a hydrophilic portion, and which is soluble in the use environment. By substantially "free from" is meant that the amount of surfactant present in the composition is less than 0.05 wt %. Preferably, the amount of the surfactant present in the nanoparticles is less than the detection limit. As discussed above, surfactants can be poorly tolerated in vivo, and thus it is preferred to avoid their use in the instant nanoparticles.

Preferably, the nanoparticles are ionized when present in an aqueous use environment. It is believed that physical stability of the nanoparticles, in the sense of not aggregating or flocculating, is related, in part, to the amount of electric charge on the nanoparticle. The charge may be either positive or negative; for the nanoparticles of the present invention comprising a bile salt, the charge is typically negative. An indirect measure of charge is zeta potential. The nanoparticles preferably have a zeta potential of less than −10 mV or greater than +10 mV (that is, the absolute value of the zeta potential is greater than 10 mV). Preferably, to reduce aggregation, the absolute value of the zeta potential is at least 20 mV, more preferably at least 30 mV, and even more preferably at least 40 mV. Zeta potential is typically calculated from the electrophoretic mobility measured by light scattering, R. J. Hunter, *Zeta Potential in Colloid Science. Principles and Applications*, Academic Press, 1981. Zeta potential may be measured using any number of commercially-available instruments, such as Brookhaven Instruments Corp. ZetaPals zeta potential analyzer.

The Drug

The drug is a "poorly water soluble drug," meaning that the drug has a solubility in water (over the pH range of 6.5 to 7.5 at 25° C.) of less than 5 mg/mL. The utility of the invention increases as the water solubility of the drug decreases. The drug may have an even lower solubility in water, such as less than about 1 mg/mL, less than about 0.1 mg/mL, and even less than about 0.01 mg/mL.

In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, anti-obesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Each named drug should be understood to include the nonionized form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Exemplary drugs suitable for use in the nanoparticles include, but are not limited to, phosphodiesterase inhibitors, such as sildenafil and sildenafil citrate; HMG-CoA reductase inhibitors, such as atorvastatin, lovastatin, simvastatin, pravastatin, fluvastatin, rosuvastatin, itavastatin, nisvastatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; calcium channel blockers, such as nifedipine, nicardipine, verapamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; carbonic anhydrase inhibitors; and glycogen phosphorylase inhibitors. Other low-solubility drugs suitable for use in the nanoparticles are disclosed in US Published patent application 2005/0031692, herein incorporated by reference.

In one embodiment, the drug is ziprasidone or a pharmaceutically acceptable form thereof.

In another embodiment, the drug is a hydrophobic non-ionizable drug. By "hydrophobic non-ionizable drug" is meant a subclass of non-ionizable drugs that are essentially water insoluble and highly hydrophobic, and are characterized by a set of physical properties, as described hereinafter. By "non-ionizable" is meant that the drug has substantially no ionizable groups. By "ionizable groups" is meant functional groups that are at least about 10% ionized over at least a portion of the physiologically relevant pH range of 1 to 8. Such groups have pKa values of about 0 to 9. Thus, hydrophobic non-ionizable drugs do not have a pKa value between 0 and 9.

The first property of hydrophobic drugs is that they are extremely hydrophobic. Log P, defined as the base 10 logarithm of the ratio of the drug solubility in octanol to the drug solubility in water, is a widely accepted measure of hydrophobicity. By "extremely hydrophobic" is meant that the Log P value of the drug is at least 4.0, preferably at least 4.5, and most preferably at least 5.0. Log P may be measured experimentally or calculated using methods known in the art. When using a calculated value for Log P, the highest value calculated using any generally accepted method for calculating Log P is used. Calculated Log P values are often referred to by the calculation method, such as C log P, A log P, and M log P. The Log P may also be estimated using fragmentation methods, such as Crippen's fragmentation method (27 J. Chem. Inf. Comput. Sci. 21 (1987)); Viswanadhan's fragmentation method (29 J. Chem. Inf. Comput. Sci. 163 (1989)); or Broto's fragmentation method (19 Eur. J. Med. Chem.-Chim. Theor. 71 (1984).

The second property of hydrophobic drugs is that they have an extremely low solubility in water over the pH range of 6.5 to 7.5 at 25° C. By "extremely low solubility in water" is meant that the solubility of the drug in water is less than 100 µg/mL. Preferably, the hydrophobic drug has a water solubility of less than 50 µg/mL, and most preferably less than 10 µg/mL.

In another embodiment the drug is a cholesteryl ester transfer protein (CETP) inhibitor. CETP inhibitors are drugs that inhibit CETP activity. The effect of a drug on the activity of CETP can be determined by measuring the relative transfer ratio of radiolabeled lipids between lipoprotein fractions, essentially as previously described by Morton in *J. Biol. Chem.* 256, 11992, 1981 and by Dias in *Clin. Chem.* 34, 2322, 1988, and as presented in U.S. Pat. No. 6,197,786, the disclosures of which are herein incorporated by reference. The potency of CETP inhibitors may be determined by performing the above-described assay in the presence of varying concentrations of the test compounds and determining the concentration required for 50% inhibition of transfer of radiolabeled lipids between lipoprotein fractions. This value is defined as the "$IC_{50}$ value." Preferably, the CETP inhibitor has an $IC_{50}$ value of less than about 2000 nM, more preferably less than about 1500 nM, even more preferably less than about 1000 nM, and most preferably less than about 500 nM.

Specific examples of CETP inhibitors include [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester; (2R)-3-[[3-(4-chloro-3-ethylphenoxy)phenyl][[3-(1,1,2,2-tetrafluoroethoxy)phenyl]methyl]amino]-1,1,1-trifluoro-2-propanol; S-[2-([[1-(2-ethylbutyl)cyclohexyl]carbonyl]amino)phenyl]2-methylpropanethioate; trans-4-[[[2-[[[[3,5-bis(trifluoromethyl)phenyl]methyl](2-methyl-2H-tetrazol-5-yl)amino]methyl]-4-(trifluoromethyl) phenyl]ethylamino]methyl]-cyclohexaneacetic acid; trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl) acetic acid methanesulfonate; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide; methyl N-(3-cyano-5-trifluoromethylbenzyl)-[6-(N'-cyclopentylmethyl-N'-ethylamino)indan-5-ylmethyl]-carbamate; methyl(3-cyano-5-trifluoromethylbenzl)-[6-(N-cyclopentylmethyl-N-ethylamino)indan-5-ylmethyl]-carbamate; ethyl 4-((3,5-bis (trifluoromethyl)phenyl)(2-methyl-2H-tetrazol-5-yl) methyl)-2-ethyl-6-(trifluoromethyl)-3,4-dihydroquinoxaline-1(2H)-carboxylate; tert-butyl 5-(N-(3,5-bis(trifluoromethyl)benzyl)acetamido)-7-methyl-8-(trifluoromethyl)-2,3,4,5-tetrahydrobenzo[b]azepine-1-carboxylate; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl-amino]-methyl}-4-trifluoromethyl-phenyl)-2-methyl-propyl]-piperidine-4-carboxylic acid; (3,5-bistrifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; the drugs disclosed in commonly owned U.S. patent application Ser. Nos. 09/918,127 and 10/066,091, the disclosures of both of which are incorporated herein by reference; and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; JP 11049743; WO 0018721; WO 0018723; WO 0018724; WO 0017164; WO 0017165; WO 0017166; EP 992496; EP 987251; WO 9835937; JP 03221376; WO 04020393; WO 05095395; WO 05095409; WO 05100298; WO 05037796; WO 0509805; WO 03028727; WO 04039364; WO 04039453; WO 0633002; and U.S. Provisional Patent Application Nos. 60/781,488 and 60/780,993, both of which were filed on Mar. 10, 2006.

Thus, in one embodiment, the CETP inhibitor is selected from the group of compounds mentioned above. In another embodiment, the CETP inhibitor is selected from the group consisting of (2R)-3-[[3-(4-chloro-3-ethylphenoxy)phenyl][[3-(1,1,2,2-tetrafluoroethoxy)phenyl]methyl]amino]-1,1,1-trifluoro-2-propanol; trans-(2R,4S)-2-(4-(4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; and pharmaceutically acceptable forms thereof.

In still another embodiment, the CETP inhibitor is (2R)-3-[[3-(4-chloro-3-ethylphenoxy)phenyl][[3-(1,1,2,2-tetrafluoroethoxy)phenyl]methyl]amino]-1,1,1-trifluoro-2-propanol.

In still another embodiment, the CETP inhibitor is trans-(2R,4S)-2-(4-{4-[(3,5-Bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide.

In another embodiment, the drug is an inhibitor of cyclooxygenase-2 (COX-2). COX-2 inhibitors are nonsteroidal anti-inflammatory drugs that exhibit anti-inflammatory, analgesic and antipyretic effects. Preferably, the COX-2 inhibitor is a selective COX-2 inhibitor, meaning that the drug is able to inhibit COX-2 without significant inhibition of cyclooxygenase-1 (COX-1). Preferably, the COX-2 inhibitor has a potency such that the concentration of drug that inhibits 50% of COX-2 enzyme in an in vitro test (i.e., the $IC_{50}$ value) is less than about 10 µM, preferably less than 5 µM, more preferably less than 2 µM. In addition, it is also preferable that the COX-2 inhibitor be selective relative to COX-1. Thus, preferably, the ratio of the $IC_{50,COX-2}$ to $IC_{50,COX-1}$ ratio for the compound is less than 0.5, more preferably less than 0.3, and most preferably less than 0.2.

Specific examples of COX-2 inhibitors include 4-(5-(4-methylphenyl)-3-(trifluoromethyl)-1H-pyrazol-1-yl)benzenesulfonamide (celecoxib); 4-(5-methyl-3-phenylisoxazol-4-yl)benzenesulfonamide (valdecoxib); N-(4-(5-methyl-3-phenylisoxazol-4-yl)phenylsulfonyl)propionamide (paracoxb); sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; 2-[(2-chloro-6-fluorophenyl)amino]-5-methyl benzeneacetic acid (lumiracoxib); 4-(3-(difluoromethyl)-5-(3-fluoro-4-methoxyphenyl)-1H-pyrazol-1-yl)benzenesulfonamide (deracoxib); 4-(4-(methylsulfonyl)phenyl)-3-phenylfuran-2(5H)-one (rofecoxib); 5-chloro-2-(6-methylpyridin-3-yl)-3-(4-(methylsulfonyl)phenyl)pyridine (etoricoxib); 2-(3,4-difluorophenyl)-4-(3-hydroxy-3-methylbutoxy)-5-(4-(methylsulfonyl)phenyl)pyridazin-3(2H)-one; (Z)-3-((3-chlorophenyl)(4-(methylsulfonyl)phenyl)methylene)-dihydrofuran-2(3H)-one; N-(2-(cyclohexyloxy)-4-nitrophenyl)methanesulfonamide; 4-Methyl-2-(3,4-dimethylphenyl)-1-(4-sulfamoyl-phenyl)-1H-pyrrole; 6-((5-(4-chlorobenzoyl)-1,4-dimethyl-1H-pyrrol-2-yl)methyl) pyridazin-3(2H)-one; 4-(4-cyclohexyl-2-methyloxazol-5-yl)-2-fluorobenzenesulfonamide (tilmacoxib); 2-(4-Ethoxyphenyl)-4-methyl-1-(4-sulfamoylphenyl)-1H-pyrrole; 4-hydroxy-2-methyl-N-(5-methyl-2-thiazolyl)-2H-1,2-benzothiazine-3-carboxamide-1,1-dioxide (meloxicam); 4-(4-chloro-5-(3-fluoro-4-methoxyphenyl)-1H-pyrazol-1-yl)benzenesulfonamide(cimicoxib), and pharmaceutically acceptable forms thereof; and the compounds disclosed in the following patents and published applications, the disclosures of which are incorporated herein by reference: U.S. Pat. No. 5,466,823, U.S. Pat. No. 5,633,272, U.S. Pat. No. 5,932,598, U.S. Pat. No. 6,034,256, U.S. Pat. No. 6,180,651, U.S. Pat. No. 5,908,858, U.S. Pat. No. 5,521,207, U.S. Pat. No. 5,691,374, WO 99/11605, WO 98/03484, and WO 00/24719.

Preferably the COX-2 inhibitor is selected from the group consisting of celecoxib; valdecoxib; paracoxb; sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; and pharmaceutically acceptable forms thereof. In one embodiment, the COX-2 inhibitor is celecoxib or pharmaceutically acceptable forms thereof.

Processes for Forming Nanoparticles

The nanoparticles may be formed by any process that results in formation of nanoparticles of drug, ethylcellulose, and a bile salt. The drug used to form the nanoparticles may be in a crystalline or non-crystalline form; however, at least 90 wt % of the drug in the resulting nanoparticles is in non-crystalline form.

One process for forming nanoparticles is an emulsification process. In this process, the drug and ethylcellulose are dissolved in an organic solvent that is immiscible with an aqueous solution in which the drug and ethylcellulose are poorly soluble, forming an organic solution. Solvents suitable for forming the solution of dissolved drug and ethylcellulose can be any compound or mixture of compounds in which the drug and the ethylcellulose are mutually soluble and which is immiscible with the aqueous solution. As used herein, the term "immiscible" means that the organic solvent has a solubility in the aqueous solution of less than about 10 wt %, preferably less than about 5 wt %, and most preferably less than about 3 wt %. Preferably, the solvent is also volatile with a boiling point of 150° C. or less. Exemplary organic solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. Preferred organic solvents are methylene chloride, ethyl acetate, benzyl alcohol, and mixtures thereof.

The bile salt is added to the aqueous solution. Generally, the amount of bile salt added to the aqueous solution will be at least 0.1 mg/mL organic solvent used in the process, but will generally be less than about 100 mg/mL organic solvent used in the process. Preferably, the amount of bile salt will range from 1 mg/mL to 50 mg/mL of organic solvent used in the process.

Once the organic solution is formed, it is then mixed with the aqueous solution and homogenized to form an emulsion of fine droplets of the water immiscible solvent distributed throughout the aqueous phase. The volume ratio of organic solution to aqueous solution used in the process will generally range from 1:100 (organic solution:aqueous solution) to 2:3 (organic solution:aqueous solution). Preferably, the organic solution:aqueous solution volume ratio ranges from 1:9 to 1:2 (organic solution:aqueous solution). The emulsion is generally formed by a two-step homogenization procedure. The solution of drug, ethylcellulose and organic solvent is first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. Preferably, the organic solvent is removed to a level that is acceptable according to The International Committee on Harmonization (ICH) guidelines. Preferably, the concentration of organic solvent in the nanoparticle suspension is less than the solubility of the organic solvent in the aqueous solution. Even lower concentrations of organic solvent are preferred. Thus, the concentration of organic solvent in the nanoparticle suspension may be less than about 5 wt %, less than about 3 wt %, less than 1 wt %, and even less than 0.1 wt %.

An alternative process to form the nanoparticles is a precipitation process. In this process, the drug and ethylcellulose are first dissolved in an organic solvent that is miscible with an aqueous solution in which the drug and ethylcellulose are poorly soluble. The resulting organic solution is mixed with the aqueous solution which contains the bile salt, causing the nanoparticles to precipitate. Solvents suitable for forming the solution of dissolved drug and ethylcellulose can be any compound or mixture of compounds in which the drug and the ethylcellulose are mutually soluble and which is miscible in the aqueous solution. Preferably, the organic solvent is volatile with a boiling point of 150° C. or less. Exemplary solvents include acetone, methanol, ethanol, tetrahydrofuran (THF), and dimethylsulfoxide (DMSO). Mixtures of solvents, such as 50% methanol and 50% acetone, can also be used, as can mixtures with water, so long as the ethylcellulose and drug are sufficiently soluble to dissolve the drug and ethylcellulose. Preferred solvents are methanol, acetone, and mixtures thereof.

The aqueous solution may be any compound or mixture of compounds in which drug and ethylcellulose are sufficiently insoluble so as to precipitate to form nanoparticles. The aqueous solution preferably comprises the bile salt and water.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of drug and ethylcellulose in the organic solution depends on the solubility of each in the organic solvent and the desired ratios of drug to ethylcellulose in the resulting nanoparticles. The organic solution may comprise from about 0.1 wt % to about 20 wt % dissolved solids. A dissolved solids content of from about 0.5 wt % to 10 wt % is preferred.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). Preferably, the organic solution:aqueous solution volume ratio ranges from about 1:20 to about 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. Preferably, the solvent is removed to a level that is acceptable according to ICH guidelines. Thus, the concentration of solvent in the nanoparticle suspension may be less than about 10 wt %, less than about 5 wt %, less than about 3 wt %, less than 1 wt %, and even less than 0.1 wt %.

Thus, in one embodiment, a process for forming nanoparticles comprises: (a) forming an organic solution comprising a poorly water soluble drug and ethylcellulose dissolved in an organic solvent, wherein the drug has a solubility in water of less than 5 mg/ml over the pH range of 6.5 to 7.5; (b) forming an aqueous solution comprising a bile salt, wherein the drug and the ethylcellulose are poorly soluble in the aqueous solution; (c) mixing the organic solution with the aqueous solution to form a first mixture; (d) removing the solvent from the first mixture to form a suspension comprising the nanoparticles and the aqueous solution, wherein (i) the nanoparticles have an average size of less than 500 nm, (ii) at least 90 wt % of the drug in the nanoparticles is non-crystalline, (iii) the drug constitutes from 0.1 wt % to 75 wt %, the ethylcellulose constitutes from 2 wt % to 85 wt %, and the bile salt constitutes from 0.5 wt % to 60 wt % of the total mass of the drug, the ethylcellulose, and the bile salt in said nanoparticles, and (iv) the drug, the ethylcellulose, and the bile salt collectively constitute at least 80 wt % of the nanoparticles.

Both the emulsion process and the precipitation process result in the formation of a suspension of the nanoparticles in the aqueous solution. In some instances it is desirable to concentrate the nanoparticles or to isolate the nanoparticles in solid form by removing some or all of the liquid from the suspension. Exemplary processes for removing at least a portion of the liquid include spray drying, spray coating, spray layering, lyophilization, evaporation, vacuum evaporation, filtration, ultrafiltration, reverse osmosis, and other processes known in the art. A preferred process is spray drying. One or more processes may be combined to remove the liquid from the nanoparticle suspension to yield a solid composition. For example, a portion of the liquids may be removed by filtration to concentrate the nanoparticles, followed by spray-drying to remove most of the remaining liquids, followed by a further drying step such as tray-drying.

When isolating the nanoparticles in solid form, it is often desirable to include a matrix material into the suspension of nanoparticles prior to removal of the liquids. The matrix material functions to help slow or prevent agglomeration of the nanoparticles as the liquids are being removed, as well as to help re-suspend the nanoparticles when the solid composition is added to an aqueous solution (e.g., an aqueous environment of use). The matrix material is preferably pharmaceutically acceptable and water soluble. Examples of matrix materials include polyvinyl pyrrolidone (PVP), trehalose, hydroxypropyl methyl cellulose (HPMC), hydroxypropyl cellulose (HPC), casein, caseinate, albumin, gelatin, acacia, lactose, mannitol, pharmaceutically acceptable forms thereof, and other matrix materials known in the art.

In one embodiment of the invention, a solid composition comprises (a) a plurality of nanoparticles comprising a poorly water-soluble drug, ethylcellulose, and a bile salt, and (b) a matrix material. As used herein, the term "solid pharmaceutical composition" means that the composition is in a solid form and substantially free of liquids. The nanoparticles are entrapped or encapsulated in the matrix material.

The presence of nanoparticles in the solid composition can be determined using the following procedure. A sample of the solid composition is embedded in a suitable material, such as an epoxy or polyacrylic acid (e.g., L R White from London Resin Co., London, England). The sample is then microtomed to obtain a cross-section of the solid composition that is about 100 to 200 nm thick. This sample is then analyzed using transmission electron microscopy (TEM) with energy dispersive X-ray (EDX) analysis. TEM-EDX analysis quantitatively measures the concentration and type of atoms larger than boron over the surface of the sample. From this analysis, regions that are rich in drug can be distinguished from regions that are rich in the matrix material. The size of the regions that are rich in drug will have an average diameter of less than 500 nm in this analysis, demonstrating that the solid composition comprises nanoparticles of drug in the matrix material. See, for example, *Transmission Electron Microscopy and Diffractometry of Materials* (2001) for further details of the TEM-EDX method.

Another procedure that demonstrates the solid composition contains nanoparticles is to administer a sample of the solid composition to water to form a suspension of the nanoparticles. The suspension is then analyzed by dynamic DLS as described herein. A solid composition of the invention will form nanoparticles having an average cumulant diameter of less than 500 nm.

A specific procedure for demonstrating the solid composition contains nanoparticles is as follows. A sample of the solid composition is added to water at ambient temperature such that the concentration of solids is less than about 1 mg/mL. The so-formed suspension is then analyzed by DLS. The solid composition contains nanoparticles if the DLS analysis results in particles having an average cumulant diameter of less than 500 nm.

A solid composition of the invention will show the presence of nanoparticles in at least one, and preferably both of the above tests.

Resuspendability

In one embodiment, solid compositions of the present invention result in improved resuspendability of the nanoparticles relative to surfactant-based stabilizers. The term "resuspendability" as used herein means the ability of the solid material, when administered to an aqueous use environment, to form a nanoparticle suspension.

The ability of the solid composition to resuspend nanoparticles when administered to an aqueous solution can be determined using the following procedures. In the first procedure, the average particle size of the re-suspended material is determined as follows. The solid composition is added to an aqueous solution, such as water, PBS, or MFD solution, to form a suspension. A sample of the solid composition is added to water at ambient temperature such that the concentration of solids is less than about 1 mg/mL. The average particle size of the nanoparticles formed during this (re)suspension is then determined by dynamic light scattering (DLS) techniques. A solid composition is said to provide good resuspendability if, upon administration to an aqueous solution, the average particle size as determined by DLS techniques is at least 50% and no more than 200% the average particle size of the nanoparticles prior to recovery of the solid composition. Preferably, the formulation provides an average particle size that is at least 67% and no more than 150% the average particle size prior to recovery of the solid composition. Even more preferably, the formulation provides an average particle size that is at least 75% and no more than 133% the average particle size prior to recovery of the solid composition.

The second procedure is known as a filter potency test. In this test the concentration of drug after passing the suspension of the nanoparticles through a filter is determined. The solid composition is added to an aqueous solution as described above. The concentration of drug in the so-formed suspension is then determined using standard techniques, such as by high-performance liquid chromatography (HPLC). Next, the suspension is filtered through a filter, and the concentration of drug in the filtered sample is determined via standard techniques. A loss in potency after filtering a sample through a filter is an indication that the nanoparticles in the sample are larger than the filter pore size. Exemplary filters that can be used in this test include a 1-μm glass fiber filter, a 0.45-μm syringe filter, and a 0.2-μm syringe filter. One skilled in the art will understand that the pore size of the filter should be selected to ensure the nanoparticles are not retained on the filter. Generally, the pore size of filter and the range of nanoparticle average diameters are given as follows:

| Filter Pore Size (μm) | Suitable Range of Nanoparticle Diameters (nm) |
|---|---|
| 1 | >250 |
| 0.45 | 150 to 300 |
| 0.2 | <200 |

A solid composition is said to provide good resuspendability if the ratio of the concentration of drug in the filtered sample is at least 60% the concentration of drug in the unfiltered sample. Preferably, the concentration of drug in the filtered sample is at least 70% the concentration of drug in the unfiltered sample. Most preferably, the concentration of drug in the filtered sample is at least 80% the concentration of drug in the unfiltered sample.

In an especially preferred embodiment, a composition provides good resuspendability in both of the tests described above.

Dosage Forms

The compositions of the present invention may be administered using any known dosage form. The nanoparticles may be formulated for administration via oral, topical, subdermal, intranasal, buccal, intrathecal, ocular, intraaural, subcutaneous spaces, intraarticular, vaginal tract, arterial and venous blood vessels, pulmonary tract or intramuscular tissue of an animal, such as a mammal and particularly a human. Oral dosage forms include: powders or granules; tablets; chewable tablets; capsules; unit dose packets, sometimes referred to in the art as "sachets" or "oral powders for constitution" (OPC); syrups; and suspensions. Parenteral dosage forms include reconstitutable powders or suspensions. Topical dosage forms include creams, pastes, suspensions, powders, foams and gels. Ocular dosage forms include suspensions, powders, gels, creams, pastes, solid inserts and implants.

In one embodiment, the compositions of the present invention are capable of improving the concentration of dissolved drug in a use environment relative to a control composition consisting essentially of the drug alone without any ethylcellulose or bile salt. In order to determine concentration enhancement in vitro, the amount of "free" drug, or solvated drug is measured. By "free" drug is meant drug which is in the form of dissolved drug or present in micelles, but which is not in the nanoparticles or any solid particles larger than 500 nm, such as precipitate. A composition of the invention provides concentration enhancement if, when administered to an aqueous use environment, it provides a free drug concentration that is at least 1.25-fold the free drug concentration provided by the control composition. Preferably, the free drug concentration provided by the compositions of the invention are at least about 1.5-fold, more preferably at least about 2-fold, and most preferably at least about 3-fold that provided by the control composition.

Alternatively, the compositions of the present invention, when administered to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when administered to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

Examples

Drugs Used in Examples

The following drugs were used in the examples described below.

Drug 1 was 4-[5-(4-methylphenyl)-3-(trifluoromethyl)-1H-pyrazol-1-yl]benzenesulfonamide, also known as celecoxib, having the structure:

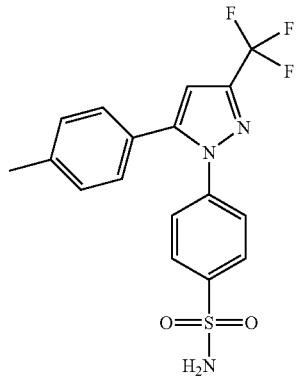

Drug 1 is a selective COX-2 inhibitor, having an $IC_{50,COX-2}$ value of about 1 µM, and an $IC_{50,COX-2}/IC_{50,COX-1}$ ratio of about 0.1. Drug 1 has a solubility in MFD solution of about 40 µg/mL, and a C Log P value of 3.75. The $T_m$ of Drug 1 is 158° C., and the $T_g$ of amorphous Drug 1 was determined by DSC analysis to be 54° C.

Drug 2 was 4-(5-methyl-3-phenyl-4-isoxazolyl)benzenesulfonamide, also known as valdecoxib, having the structure:

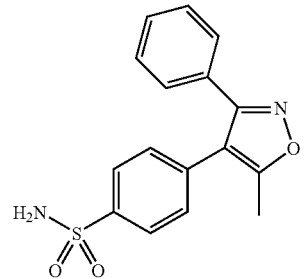

Drug 2 is a selective COX-2 inhibitor, having an $IC_{50,COX-2}$ value of about 1 µM, and an $IC_{50,COX-2}/IC_{50,COX-1}$ ratio of about 0.05. Drug 2 has a solubility in water of about 10 µg/mL, and a C Log P value of about 3.0. The $T_g$ of non-crystalline Drug 2 was determined by DSC analysis to be 55° C., while the $T_m$ of crystalline Drug 2 was 170° C.

Drug 3 was [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, having the structure:

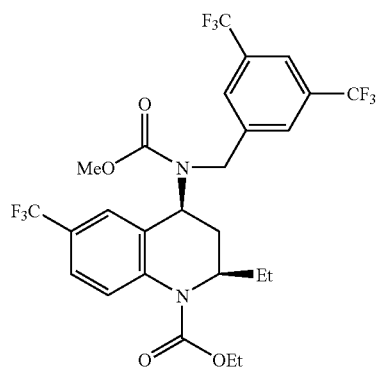

Drug 3 is a potent CETP inhibitor having an $IC_{50}$ value of about 50 nM. Drug 3 has a solubility in water of less than 0.1 μg/mL, and a C Log P value of 7.6. The $T_m$ of Drug 3 is 99° C., and the $T_g$ was determined by DSC analysis to be 29° C.

Drug 4 was [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, having the structure:

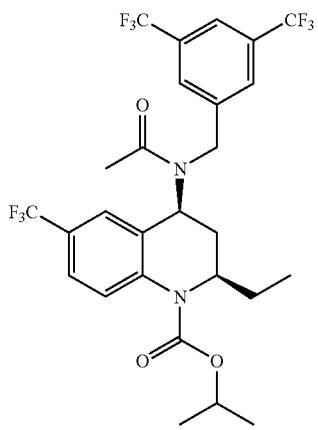

Drug 4 has a solubility in MFD solution of about 11 μg/mL, and a C Log P value of about 6.6. The $T_m$ of Drug 4 is 111° C., and the $T_g$ was determined by DSC analysis to be about 45° C.

Drug 5 was 2-(2-chloro-4-iodophenylamino)-N-cyclopropylmethoxy-3,4-difluorobenzamide, having the structure:

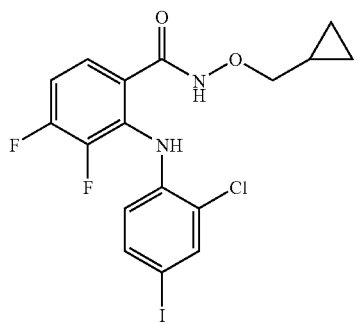

Drug 5 has an aqueous solubility of about 0.03 μg/mL, and a C Log P value of 5.9. The $T_m$ of Drug 5 is 177° C., and the $T_g$ was determined by DSC analysis to be about 46° C.

Example 1

Nanoparticles containing celecoxib ("Drug 1") were prepared as follows. First, 96 mg celecoxib and 336 mg ethylcellulose (ETHOCEL® Std. 4) were dissolved in 6 mL methylene chloride to form an organic solution. Next, 48 mg sodium taurocholate (NaTC) was dissolved in 24 mL deionized water to form an aqueous solution. The organic solution was then poured into the aqueous solution and emulsified for 3 min using a Kinematica Polytron 3100 rotor/stator (Kinematica A G, Lucerne, Switzerland) at 10,000 rpm (high-shear mixing). The solution was further emulsified using a Microfluidizer (Microfluidics [Newton, Mass.] model M-110S F12Y with ice bath and cooling coil), for 6 minutes (high-pressure homogenization). The methylene chloride was removed from the emulsion using a rotary evaporator, resulting in an aqueous suspension of nanoparticles, with a composition mass ratio of 20:70:10 celecoxib:ethylcellulose:NaTC.

Light Scattering Analysis

The particle size of the nanoparticles in the aqueous suspension was determined using dynamic light scattering (DLS) as follows. First, the aqueous suspension was filtered using a 1 μm glass membrane filter (Anatop filter, Whatman), and poured into a cuvette. Dynamic light-scattering was measured using a Brookhaven Instruments (Holtsville, N.Y.) BI-200SM particle size analyzer with a BI-9000AT correlator. The sums of exponentials from the autocorrelation functions were analyzed using CONTIN software to extract size distributions from the samples. The cumulant diameter of the nanoparticles in suspension was 73 nm, with a polydispersity of 0.17.

Isolation of Solid Compositions

A solid composition of the present invention was formed as follows. First, 120 mg of the matrix material sodium caseinate (5 mg/mL) was added to the aqueous nanoparticle suspension, resulting in a 16:56:8:20 mass ratio of celecoxib:ethylcellulose:NaTC:casein.

The resulting nanoparticle suspension was spray dried as follows. The aqueous nanoparticle suspension was added to a reservoir and pumped to a two fluid nozzle located in a spray-drying chamber, using an HPLC pump (model 515, Waters Corp., Milford, Mass.) at a flow rate of about 0.15 g/min. The spray-drying chamber consisted of two sections: a straight-side section (top), and a cone section (bottom). The top of the straight-side section was equipped with a spray-solution inlet. The spray solution was sprayed through the spray-solution inlet using the two-fluid nozzle, into the straight-side section of the spray-drying chamber. The straight-side section had a diameter of 10 cm and a length of 19 cm.

Drying gas (nitrogen) entered the cone section through a drying-gas inlet at a flow of about 1.0 SCFM and an inlet temperature of about 120° C. The flow rate of drying gas and spray solution were selected such that the atomized spray solution was sufficiently dry by the time it reached the walls of the spray-drying chamber that it did not stick to the walls. The diameter of the cone section at the top was 10 cm, and the distance from the top of the cone section to the bottom was 19 cm. At the bottom of the cone section was a 4.7-cm diameter outlet port, fitted with a 0.8 μm nylon filter (Magna, GE Osmonics, Minnetonka, Minn.) supported by a metal screen. The spray dried composition was collected on the filter, and evaporated solvent and drying gas were removed from the spray-drying chamber through the outlet port.

Nanoparticle Resuspension

The solid composition of Example 1 was resuspended by adding a 25 mg sample to 1.1 mL deionized water. DLS analysis showed that the average cumulant diameter of the nanoparticle suspension was 107 nm, with a polydispersity of 0.20. This demonstrates that a small particle size can be obtained after isolation of the solid composition, followed by resuspension.

Filter Potency

A filter potency test was used to characterize the resuspended nanoparticles of Example 1. A 100 μL sample of the aqueous nanoparticle suspension of Example 1 was added to 1 mL 80/20 methanol/acetonitrile, and the concentration of drug in solution was analyzed by HPLC. Next, the suspension was filtered using a 0.2 μm filter and diluted in 80/20 methanol/acetonitrile for HPLC analysis.

Potencies of the nanoparticle suspensions are shown in Table 1. The results in Table 1 show that 94% of the nanoparticle suspension potency is maintained following filtration by a 0.2 μm filter. This indicates that most of the nanoparticles in suspension remain small and unagglomerated.

TABLE 1

| Sample | Potency Unfiltered (mg/mL) | Potency 0.2 μm filtered (mg/mL) | Potency Retained (%) |
| --- | --- | --- | --- |
| Example 1 | 3.4 | 3.2 | 94 |

Examples 2-8

The nanoparticles of Examples 2 to 8 were made containing celecoxib, ethylcellulose, and NaTC, using the procedures presented in Example 1 with the exceptions noted in Table 2. In each case, the methylene chloride was removed using a rotary evaporator, to obtain the aqueous suspensions of nanoparticles.

The average diameter of the nanoparticles was measured by DLS using the procedures described in Example 1. The results are presented in Table 3. These data show that small nanoparticles can be made using the composition of the present invention.

TABLE 2

| Example | Organic Solution Volume (mL) | Drug 1 (mg) | Ethylcellulose (mg) | Aqueous Solution Volume (mL) | Bile Salt (mg) | Pre-Emulsification Time* (min) | Emulsification Time** (min) |
| --- | --- | --- | --- | --- | --- | --- | --- |
| 1 | 6 | 96 | 336 | 24 | 48 | 3 | 6 |
| 2 | 7.5 | 240 | 300 | 30 | 30 | 3 | 6 |
| 3 | 300 | 8,000 | 10,000 | 1000 | 2000 | 3 | 6 |
| 4 | 7.5 | 120 | 420 | 30 | 60 | 3 | 6 |
| 5 | 10.6 | 12.6 | 109 | 20 | 13.5 | 5 | 5 |
| 6 | 10.7 | 30.1 | 90.1 | 20 | 14.1 | 5 | 5 |
| 7 | 10.6 | 60.6 | 61.1 | 20 | 13.9 | 5 | 5 |
| 8 | 5.3 | 20.1 | 30.2 | 20 | 40 | 5 | 3 |

*Using Kinematica Polytron 3100 rotor/stator at 10,000 rpm
**Using microfluidizer

TABLE 3

| Example | Formulation (drug:ethylcellulose:NaTC) (wt:wt:wt) | Average Cumulant Diameter (nm) | Polydispersity |
| --- | --- | --- | --- |
| 1 | 20:70:10 | 73 | 0.17 |
| 2 | 42:53:5 | 69 | 0.19 |
| 3 | 42:53:5 | 90 | 0.08 |
| 4 | 21:74:5 | 63 | 0.08 |
| 5 | 9:77:14 | 120 | 0.19 |
| 6 | 22:64:14 | 117 | 0.09 |
| 7 | 43:43:14 | 107 | 0.19 |
| 8 | 29:43:28 | 76 | 0.45 |

Isolation of Solid Compositions of Example 3

Solid compositions of the invention were prepared as follows. First, 6.67 mg sodium caseinate was added to the aqueous nanoparticle suspension of Example 3. The nanoparticle suspension of Example 3 had a mass ratio of 30:37.5:7.5:25 celecoxib:ethylcellulose:NaTC:casein.

The resulting suspension was spray dried using the following procedure. The nanoparticle suspension was pumped to a Niro type XP Portable Spray-Drier with a Liquid-Feed Process Vessel ("PSD-1"), equipped with a pressure nozzle (Schlick 1.0; Dusen Schlick, GmbH of Untersiemau, Germany). The PSD-1 was equipped with 9-inch and 4-inch chamber extensions. The chamber extensions were added to the spray drier to increase the vertical length of the dryer. The added length increased the residence time within the drier, which allowed the product to dry before reaching the angled section of the spray dryer. The nanoparticle suspension was pumped to the spray drier at about 20 g/min at a pressure of 175 psig. Drying gas (nitrogen) was introduced into the chamber at an inlet temperature of 90° C. The evaporated solvent and drying gas exited the spray drier at a temperature of 50° C. The resulting solid composition was collected in a cyclone.

Nanoparticle Resuspension

The solid composition of Example 3 was resuspended by adding a 37 mg sample to 2 mL deionized water. DLS analysis showed that the average cumulant diameter of the nanoparticles of Example 12 was 88 nm, with a polydispersity of 0.19.

The solid composition of Example 3 was stored in a sealed container at room temperature for 66 days to evaluate storage stability of the nanoparticles in dried form. The effect of storage on nanoparticle agglomeration was determined by resuspending the aged sample and analyzing the particle size in the suspension. The aged solid compositions of Example 3 were resuspended by adding a 25 mg sample to 1 mL deionized water. The average cumulant diameter of the nanoparticles of Example 3 was 110 nm, with a polydispersity of 0.02. This demonstrates successful resuspension of the nanoparticles, maintaining small particle size, and storage of solid compositions without particle agglomeration.

Nanoparticle Dissolution Test of Examples 5-7

The dissolution rate of celecoxib from the nanoparticles of Examples 5, 6, and 7 were measured using the following dissolution test. The aqueous suspensions of Examples 5, 6, and 7 (635 μL, 266 μL, and 132 μL, respectively) were added to 10 mL PBS containing 0.5 wt % NaTC/POPC (model fasted duodenal solution, "MFDS") in glass vials. The glass vials were stirred at ambient temperature, and 500 μL aliquots were removed at 0.5, 1, 2, 3, and 5 minutes. The aliquots were centrifuged for 5 minutes at 12,000 rpm using a 100,000-dalton molecular-weight cutoff centrifuge tube filter, and the supernatant was diluted 1:1 with dimethylsulfoxide. The samples were assayed by high-performance liquid chromatography (HPLC). Crystalline drug alone was tested for comparison. The concentration of celecoxib measured at each interval was essentially the same, so the concentration after 1 minute is shown in Table 4. The celecoxib dissolution increases with drug loading, and is much faster than that of crystalline drug alone.

TABLE 4

| Suspension Sample | Celecoxib Concentration at 1 minute (μg/mL) |
| --- | --- |
| Crystalline celecoxib | 0.7 |
| Example 5 9:77:14 celecoxib:ethylcellulose:NaTC | 4.2 |
| Example 6 22:64:14 celecoxib:ethylcellulose:NaTC | 9.4 |
| Example 7 43:43:14 celecoxib:ethylcellulose:NaTC | 20.9 |

Nanoparticle Suspension Stability of Example 8

The nanoparticle suspension of Example 8 was allowed to stand unmixed for 9 days (ambient conditions) to measure stability. DLS analysis showed that the cumulant diameter of the nanoparticles after 9 days was 84 nm, with a polydispersity of 0.35. These results demonstrate that the nanoparticle suspension is stable for at least 9 days with no measurable particle agglomeration.

Example 9

Nanoparticles containing valdecoxib ("Drug 2") were prepared using the procedures outlined in Example 1 with the following exceptions. The organic solution consisted of 30.2 mg valdecoxib and 90.1 mg ethylcellulose dissolved in 9.7 mL methylene chloride to form an organic solution. The aqueous solution consisted of 30.3 mg sodium glycocholate ("NaGly"; available from Sigma) dissolved in 20 mL deionized water. The organic solution was then poured into the aqueous solution and emulsified for 5 min using a Kinematica Polytron 3100 rotor/stator at 10,000 rpm (high-shear mixing). The solution was further emulsified using a Microfluidizer (Microfluidics model M-110L F12Y with Z chamber, ice bath and cooling coil), with an inlet pressure of 65 psi and a final pressure of 12,500 psi, for 5 minutes. The methylene chloride was removed from the emulsion using a rotary evaporator, resulting in an aqueous suspension of nanoparticles. DLS analysis of the aqueous suspension was performed using the procedures described in Example 1 and showed that the cumulant diameter of the nanoparticles was 72 nm, with a polydispersity of 0.16.

Nanoparticle Suspension Stability

The nanoparticle suspension of Example 9 was allowed to stand unmixed for 18 days (ambient conditions) to measure stability. DLS analysis showed that the cumulant diameter of the nanoparticles after 18 days was 66 nm, with a polydispersity of 0.18. These results demonstrate that the nanoparticle suspension is stable for at least 18 days with no measurable particle agglomeration.

Isolation of Solid Composition

The nanoparticles of Example 9 were isolated in dried powder form as follows. To a 5-mL sample of the suspension of nanoparticles of Example 9 was added 250 mg trehalose. The resulting suspension was lyophilized overnight to obtain a dry powder.

Control 1

Nanoparticles Without Bile Salt

As a control, nanoparticles were prepared containing valdecoxib and the ethylcellulose, but without a bile salt. To form Control 1 nanoparticles, 40.6 mg valdecoxib and 123.8 mg ethylcellulose were dissolved in 5 mL methylene chloride to form an organic solution. The organic solution was then poured into 20 mL deionized water, and emulsified using a Kinematica Polytron 3100 rotor/stator, and further emulsified using a Microfluidizer. The methylene chloride was removed from the emulsion using a rotary evaporator, resulting in an aqueous suspension of nanoparticles. The aqueous suspension was analyzed using DLS. The cumulant diameter of the nanoparticles was 815 nm, with a polydispersity of 0.41. Visual observation of the aqueous suspension confirmed large agglomerated and stringy material. These results show that nanoparticles made without a bile salt do not provide a stable formulation.

Example 10

Nanoparticles containing valdecoxib were prepared as described in Example 9 with the following exceptions. The organic solution consisted of 180.1 mg valdecoxib and 540.0 mg ethylcellulose dissolved in 59 mL methylene chloride. The aqueous solution consisted of 11.9 mg NaGly dissolved in 120 mL deionized water. The organic solution was then poured into the aqueous solution and emulsified as described for Example 1, except that the high-pressure homogenization time was 2 minutes. Following methylene chloride removal using a rotary evaporator, 2.4 g trehalose and 588.2 mg sodium glycocholate were added to the aqueous nanoparticle suspension, and the suspension was filtered using a 1 μm glass filter.

The nanoparticle suspension was spray-dried using the following procedure. The suspension was pumped to a spray-drier equipped with a pressure nozzle (Schlick 1; Dusen Schlick, GmbH of Untersiemau, Germany), at about 15 g/min. Drying gas (i.e., nitrogen) was delivered into the spray drier at 425 g/min with an inlet temperature of 210° C. The water vapor and drying gas exited the spray drier at a temperature of 45° C. The nanoparticles of Example 10 were collected in dried powder form.

Differential Scanning Calorimetry

The dried nanoparticles of Example 10 were analyzed using modulated differential scanning calorimetry (MDSC) initially, and after storage for 8 months at room temperature. The sample pans were crimped and sealed at ambient temperature and humidity, then loaded into a Thermal Analysis Q1000 DSC equipped with an autosampler. The samples were heated by modulating the temperature at ±1.5° C./min, and ramping at 2.5° C./min to about 200° C. The glass transition temperature ($T_g$) of the nanoparticles of Example 10 was found to be 56.3° C. initially, and 54.5° C. after storage for 8 months. The $T_g$ of amorphous valdecoxib is 55° C. The DSC results indicate that valdecoxib in the nanoparticles of Example 10 is initially in the amorphous form, and the amorphous form is stable for at least 8 months.

PXRD Evaluation

The nanoparticles of Example 10 were examined using powder x-ray diffraction (PXRD) with a Bruker AXS D8 Advance diffractometer to determine the amorphous character of the drug in the nanoparticles. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The x-ray source (KCu$_\alpha$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 40°. FIG. 1 is the diffraction pattern for the nanoparticles of Example 10, which showed only an amorphous halo, with no sharp peaks characteristic of crystalline drug. These data indicate that the drug in the nanoparticles of Example 10 is in a non crystalline form.

Example 11

Nanoparticles containing valdecoxib were prepared using the procedures of Example 9 with the following exceptions. The organic solution consisted of 61.3 mg valdecoxib and 182.0 mg ethylcellulose dissolved in 19.6 mL methylene chloride. The aqueous solution consisted of 201.1 mg NaGly dissolved in 40 mL deionized water. Following methylene chloride removal using a rotary evaporator, the aqueous suspension was analyzed using DLS as described in Example 1. The cumulant diameter was found to be 37 nm, with a polydispersity of 0.16.

Isolation of Solid Composition

A portion of the nanoparticle suspension was spray-dried using the following procedure. First, 0.4 g trehalose was added to a 20 mL aliquot of the aqueous suspension, and the suspension was filtered using a 1 μm glass filter. The suspension was pumped into a "mini" spray-drying apparatus via a Cole Parmer 74900 series rate-controlling syringe pump at a rate of 0.1 ml/min. The suspension was atomized through a Spraying Systems Co. two-fluid nozzle, Model No. SU1A using a heated stream of nitrogen at a flow rate of 1 SCFM. The suspension was sprayed into an 11-cm diameter stainless steel chamber. The heated gas entered the chamber at an inlet temperature of 100° C. and exited at ambient temperature. The resulting material was collected in dried powder form, and stored in a vacuum desiccator.

Measurement of Free Drug

The amount of free drug provided by a suspension of the nanoparticles of Example 11 was measured using the following procedure. Following rotary evaporation of the methylene chloride (prior to spray-drying), 200 μL of the aqueous nanoparticle suspension of Example 11 was centrifuged using a 100,000-dalton molecular-weight cutoff centrifuge tube filter, and 50 μL of the supernatant was added to 250 μL DMSO. The sample was assayed by HPLC. As shown in Table 5, free drug is enhanced 6.6-fold in the suspension containing the valdecoxib nanoparticles of Example 11, relative to crystalline drug.

TABLE 5

| Suspension Sample | Average Particle Size (nm) | Free Drug (μg/mL) |
|---|---|---|
| Crystalline Valdecoxib | >1000 | 11 |
| Example 11 | 37 | 73 |

PXRD Evaluation

Figure 2:
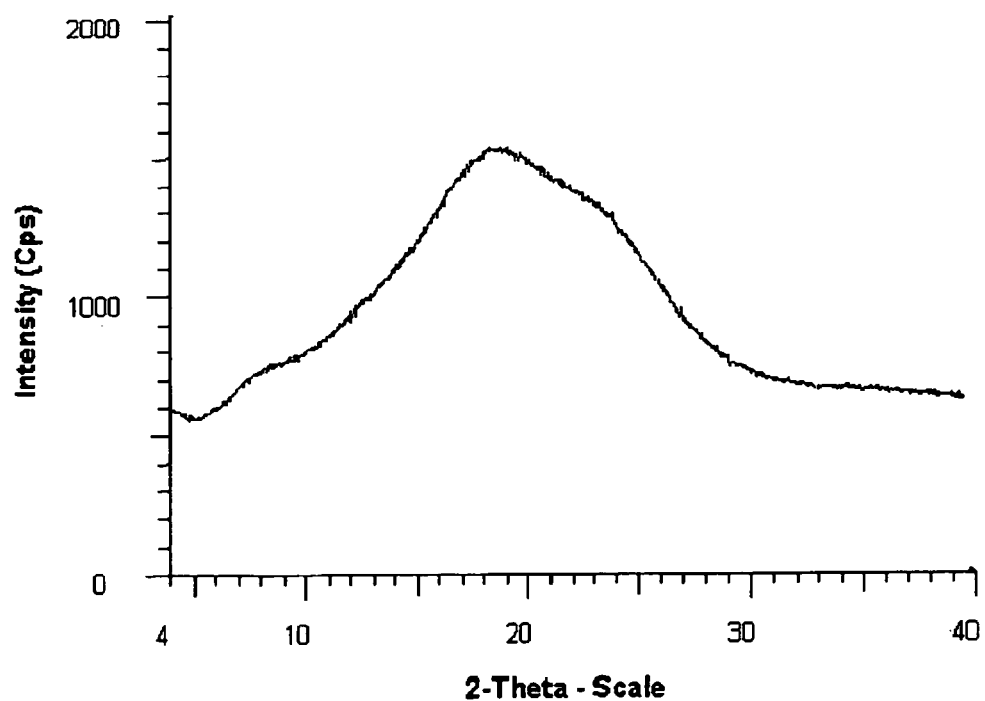
FIG. 2. is the PXRD diffraction pattern of the nanoparticles of Example 11.

The spray-dried composition of Example 11 was examined using powder x-ray diffraction (PXRD) as described for Example 10. FIG. 2 is a diffraction pattern of the solid composition of Example 11, which shows only an amorphous halo. These data indicate that the drug in the nanoparticles of Example 11 is in a non-crystalline form.

Nanoparticle Resuspension

The spray-dried composition of Example 11 was resuspended by adding 44 mg dried composition to 1 mL Hank's balanced buffer (available from HyClone Corp., Logan, Utah), to obtain a resuspension potency of about 2 mgA/mL. The suspension was vortexed 15 seconds, then analyzed using DLS. The average cumulant diameter was found to be 74 nm, with a polydispersity of 0.36. This demonstrates that a small particle size can be maintained after isolation of the nanoparticles in dry powder form, followed by resuspension.

Nanoparticle Resuspension Stability

The resuspended nanoparticles were allowed to stand unmixed for 5 days at ambient conditions. DLS analysis showed that the average cumulant diameter of the resuspended nanoparticles after 5 days was 35 nm, with a polydispersity of 0.19. These results demonstrate that the nanoparticle suspensions are stable for at least 5 days with no measurable particle agglomeration.

Example 12

Nanoparticles containing valdecoxib were prepared using the procedures described in Example 9 with the following exceptions. The organic solution consisted of 180.3 mg valdecoxib and 540.0 mg ethyl cellulose dissolved in 59 mL methylene chloride. The aqueous solution consisted of 600.1 mg NaGly dissolved in 120 mL deionized water. The organic solution was then poured into the aqueous solution and emulsified as described for Example 9, except that the high-pressure homogenation time was 10 minutes. Following methylene chloride removal using a rotary evaporator, the aqueous suspension analyzed using DLS as described above. The average cumulant diameter was found to be 44 nm, with a polydispersity of 0.14. Next, 2.4 g trehalose was added to the aqueous nanoparticle suspension, and the suspension was filtered using a 1 μm glass filter. The nanoparticle suspension was spray-dried as described in Example 10.

Measurement of Free Drug

The amount of free drug provided by a suspension of the nanoparticles of Example 12 was measured as follows. The suspension was formed by adding approximately 30 mg of the spray-dried composition 500 μL dextrose solution in an HPLC vial, and sonicating for 20 minutes. A 250 μL sample of the nanoparticle suspension was centrifuged for 5 minutes at 12,000 rpm using a 100,000-dalton molecular-weight cutoff centrifuge tube filter, and 20 μL of the supernatant was added to 500 μL DMSO. The sample was assayed by HPLC. As shown in Table 6, free drug is enhanced 7.3-fold in the suspension containing the valdecoxib nanoparticles of Example 12 relative to crystalline drug.

TABLE 6

| Suspension Sample | Average Particle Size (nm) | Free Drug (μg/mL) |
|---|---|---|
| Crystalline Valdecoxib | — | 11 |
| Example 12 | 44 | 80 |

Nanoparticle Dissolution Test

The dissolution rate of valdecoxib from nanoparticles of Example 12 was measured using the dissolution test as follows. The spray-dried composition of Example 12 were added to Hank's buffer to obtain a valdecoxib concentration of about 1 mgA/mL. The suspension was diluted to 10 μg/mL by adding 0.2 mL suspension to 20 mL buffer. The diluted suspension was placed on a shaker table in a 37° C. chamber, and aliquots were removed at 2, 5, and 10 minutes. The aliquots were centrifuged for 5 minutes at 12,000 rpm using a 30,000-dalton molecular-weight cutoff centrifuge tube filter, and 100 μL of the supernatant was added to 250 μL acetonitrile. The samples were assayed by HPLC. Crystalline drug alone was tested for comparison. The dissolution rate (percent of total drug released per minute) is shown in Table 7. The dissolution rate for nanoparticles of the invention was 3.6 times that of crystalline drug alone.

TABLE 7

| Suspension Sample | Dissolution Rate (%/min) |
|---|---|
| Crystalline Valdecoxib | 5.0 |
| Example 12 | 18.2 |

Examples 13-16

Nanoparticles containing Drug 3 were prepared using the procedures described in Example 1 with the following exceptions. For the nanoparticles of Example 13, the organic solution consisted of 94.397 mg Drug 3 and 94.592 mg ethylcellulose dissolved in 5 mL methylene chloride, and the aqueous solution consisted of 11.846 mg NaTC dissolved in 20 mL deionized water. For the nanoparticles of Example 14, the organic solution consisted of 141.634 mg Drug 3 and 47.379 mg ethylcellulose dissolved in 5 mL methylene chloride, and the aqueous solution consisted of 11.904 mg NaTC dissolved in 20 mL deionized water. For the nanoparticles of Example 15, the organic solution consisted of 111.538 mg Drug 3 and 66.938 mg ethylcellulose dissolved in 5 mL methylene chloride, and the aqueous solution consisted of 22.210 mg NaTC dissolved in 20 mL deionized water. For the nanoparticles of Example 16, the organic solution consisted of 80 mg Drug 3 and 80 mg ethylcellulose dissolved in 5 mL methylene chloride, and the aqueous solution consisted of 40 mg NaTC dissolved in 20 mL deionized water. The methylene chloride was removed from the emulsions using a rotary evaporator, resulting in aqueous suspensions of nanoparticles.

Light Scattering Analysis

DLS analysis of the aqueous suspensions was performed as described in Example 1 and the results are presented in Table 8. The suspensions were also allowed to stand unmixed for 24 hours at ambient conditions and the diameter of the nanoparticles was again measured by DLS. The results, shown in Table 8, indicate that no significant agglomeration of the nanoparticles had occurred.

TABLE 8

| Sample | Initial | | After Storage for 24 Hours Ambient | |
|---|---|---|---|---|
| (wt:wt:wt Drug 3:ethylcellulose:NaTC) | Diameter (nm) | Polydispersity | Diameter (nm) | Polydispersity |
| Example 13 (47:47:6) | 99 | 0.22 | 101 | 0.19 |
| Example 14 (71:23:6) | 101 | 0.21 | 104 | 0.16 |
| Example 15 (56:33:11) | 78 | 0.26 | 81 | 0.27 |
| Example 16 (40:40:20) | 71 | 0.30 | 77 | 0.33 |

Example 17

Nanoparticles containing Drug 4 were prepared using the procedures described in Example 1 with the following exceptions. For the nanoparticles of Example 17, the organic solution consisted of 20 mg Drug 4 and 30 mg ethylcellulose dissolved in 4 mL methylene chloride, while the aqueous solution consisted of 40 mg NaTC dissolved in 20 mL deionized water. The organic solution was then poured into the aqueous solution and emulsified as described for Example 1, except that the high shear mixing time was reduced to 2 minutes. Following methylene chloride removal using a rotary evaporator, the aqueous suspension was added to a cuvette filled with deionized water and analyzed using DLS. The average cumulant diameter was found to be 147 nm with polydispersity of 0.40.

Control 2

Nanoparticles containing Drug 4 were prepared using the procedures described for Example 17, except that they contained sodium lauryl sulfate (SLS) surfactant rather than a bile salt. For the nanoparticles of Control 2, 20 mg Drug 4 and 30 mg ethylcellulose were dissolved in 4 mL methylene chloride to form an organic solution. Next, 40 mg SLS was dissolved in 20 mL deionized water to form an aqueous solution. The organic solution was then poured into the aqueous solution and emulsified as described for Example 1, except that the high shear mixing time was reduced to 2 minutes. Following methylene chloride removal using a rotary evaporator, the aqueous suspension was added to a cuvette filled with deionized water and analyzed using DLS. The cumulant diameter immediately after formation of the nanoparticles was found to be 215 nm.

The nanoparticle suspensions of Example 17 and Control 2 were allowed to stand unmixed for 4 days (ambient conditions) to measure stability. The results of DLS analysis before and after storage are presented in Table 9 and show that the nanoparticles of the invention remained small, showing no significant agglomeration, while the nanoparticles of Control 2 showed a marked increase in diameter, indicating agglomeration was occurring.

TABLE 9

| | Before Storage | | After Storage 4 Days, Ambient Conditions | |
|---|---|---|---|---|
| Sample | Cumulant Diameter (nm) | Polydispersity | Cumulant Diameter (nm) | Polydispersity |
| Example 17 | 147 | 0.40 | 158 | 0.34 |
| Control 2 | 215 | 0.11 | 529 | 0.47 |

Examples 18-20

Nanoparticles were made containing Drug 4 using the procedures described in Example 1 with the following exceptions. For the nanoparticles of Example 18, the organic solution consisted of 12.0 mg Drug 4 and 108.4 mg ethylcellulose dissolved in 11 mL methylene chloride, while the aqueous solution consisted of 19.8 mg NaTC dissolved in 20 mL deionized water. For Example 19, the organic solution consisted of 30.1 mg Drug 4 and 90.2 mg ethylcellulose dissolved in 11 mL methylene chloride, while the aqueous solution consisted of 20 mg NaTC dissolved in 20 mL deionized water. For Example 20, the organic solution consisted of 59.7 mg Drug 4 and 66.0 mg ethylcellulose dissolved in 11 mL methylene chloride, while the aqueous solution consisted of 19.4 mg NaTC dissolved in 20 mL deionized water. In all cases, the methylene chloride was removed from the emulsions using a rotary evaporator, resulting in aqueous suspensions of nanoparticles.

DLS analysis of the aqueous suspensions was performed as described in Example 1 and the results are presented in Table 10. The suspensions were also allowed to stand unmixed for 3 days at ambient conditions and the diameter of the nanoparticles was again measured by DLS. The results, shown in Table 10, indicate that no significant agglomeration of the nanoparticles had occurred.

TABLE 10

| | Initial | | After Storage for 3 Days Ambient | |
|---|---|---|---|---|
| Sample | Cumulant Diameter (nm) | Polydispersity | Cumulant Diameter (nm) | Polydispersity |
| Example 18 | 102 | 0.15 | 102 | 0.13 |
| Example 19 | 93 | 0.18 | 92 | 0.16 |
| Example 20 | 91 | 0.12 | 93 | 0.13 |

Examples 21-24

Nanoparticles of Drug 5 were made using the procedures described in Example 1 with the following exceptions. For the nanoparticles of Example 21, the organic solution consisted of 3.9 mg Drug 5 and 76.1 mg ethylcellulose dissolved in 11 mL methylene chloride, while the aqueous solution consisted of 21.7 mg NaTC dissolved in 20 mL deionized water. For the nanoparticles of Example 22, the organic solution consisted of 7.9 mg Drug 5 and 72.0 mg ethylcellulose dissolved in 11 mL methylene chloride, while the aqueous solution consisted of 19.9 mg NaTC dissolved in 20 mL deionized water. For the nanoparticles of Example 23, the organic solution consisted of 20.0 mg Drug 5 and 72.5 mg ethylcellulose dissolved in 11 mL methylene chloride, while the aqueous solution consisted of 23.0 mg NaTC dissolved in 20 mL deionized water. For the nanoparticles of Example 24, the organic solution consisted of 28.4 mg Drug 5 and 51.9 mg ethylcellulose dissolved in 11 mL methylene chloride, while the aqueous solution consisted of 20.7 mg NaTC dissolved in 20 mL deionized water. The methylene chloride was removed from the emulsions using a rotary evaporator, resulting in aqueous suspensions of nanoparticles.

DLS analysis of the nanoparticles of Examples 21-24 was performed before and after storage for 18 or 19 days unmixed at ambient conditions, with the results shown in Table 11. These results demonstrate that the nanoparticle suspensions are stable for at least 18 days with no significant particle agglomeration.

TABLE 11

| | | | | After Storage | |
|---|---|---|---|---|---|
| Sample | Initial | | Time at | | |
| (wt:wt:wt Drug 5:ethylcellulose:NaTC) | Diameter (nm) | Polydispersity | Ambient (days) | Diameter (nm) | Polydispersity |
| Example 21 3.8:74.8:21.4 | 93 | 0.17 | 19 | 95 | 0.14 |
| Example 22 7.9:72.1:20.0 | 90 | 0.17 | 19 | 93 | 0.11 |
| Example 23 17.3:62.8:19.9 | 90 | 0.22 | 18 | 83 | 0.14 |
| Example 24 28.1:51.4:20.5 | 138 | 0.35 | NA* | NA | NA |

*NA = not analyzed

Nanoparticle Dissolution Test

The dissolution rate of Drug 5 from nanoparticles of Examples 21-24 was measured using the following dissolution test. For these tests, 2 mL samples of each nanoparticle suspension were added to scintillation vials containing 8 mL PBS with 2.0 wt % NaTC/POPC, to obtain a Drug 5 concentration of about 30 μgA/mL. The vials were placed on a shaker table in a 37° C. chamber, and aliquots were removed at 1, 6, 11, 20, 30, and 60 minutes. The aliquots were centrifuged for 5 minutes at 12,000 rpm using a 100,000-dalton molecular-weight cutoff centrifuge tube filter, and the supernatant was added to methanol for HPLC analysis. The concentration of Drug 5 in each sample is shown in Table 12. The dissolution of Drug 5 from nanoparticles of the invention increased with increasing drug loading.

TABLE 12

| Time (min) | Drug 5 released (wt %) | | | |
| --- | --- | --- | --- | --- |
| | Example 21 | Example 22 | Example 23 | Example 24 |
| 1 | 53 | 72 | 86 | 93 |
| 6 | 59 | 77 | 90 | 94 |
| 11 | 62 | 79 | 90 | 94 |
| 20 | 65 | 82 | 92 | 96 |
| 30 | 65 | 82 | 91 | 95 |
| 60 | 66 | 83 | 92 | 95 |

Example 25

Nanoparticles containing Drug 4 were prepared as follows. First, 120 mg Drug 4 and 420 mg ethylcellulose were dissolved in 7.5 mL methylene chloride to form an organic solution. Next, 60 mg NaTC was added to 30 mL deionized water to form an aqueous solution. The organic solution was then poured into the aqueous solution and emulsified as described in Example 1. The methylene chloride was removed from the emulsion using a rotary evaporator, resulting in an aqueous suspension of nanoparticles, with a composition ratio of 20:70:10 Drug 4:ethylcellulose:NaTC. DLS analysis showed that the average cumulant diameter of the nanoparticle suspension was 64 nm, with a polydispersity of 0.20.

Isolation of Solid Compositions

Sodium caseinate was added to the nanoparticle suspension of Example 25, resulting in a nanoparticle suspension consisting of 16:56:8:20 Drug 4:ethylcellulose:NaTC:casein. This suspension was then spray-dried as described in Example 1, resulting in the formation of a solid composition of the invention.

Nanoparticle Resuspension

The solid composition of Example 25 was resuspended by adding 25 mg of sample to 1 mL deionized water. DLS analysis showed that the average cumulant diameter of the nanoparticle suspension was 143 nm, with a polydispersity of 0.30. This demonstrates that a small particle size can be maintained after isolation of the nanoparticles in dry powder form, followed by resuspension.

Filter Potency

A filter potency test was used to characterize the resuspended nanoparticles of Example 25. First, a 50 μL sample of the aqueous nanoparticle suspension was added to 1 mL methanol, and the concentration of drug in solution was analyzed by HPLC. Next, the suspension was filtered using a 0.2 μm filter and diluted in methanol for HPLC analysis.

Potencies of the nanoparticle suspensions are shown in Table 13. The results in Table 13 show that 98% of the nanoparticle suspension potency is maintained following filtration of the resuspended nanoparticles of Example 25 using a 0.2 μm filter. This indicates that most of the nanoparticles in suspension remain small and unagglomerated.

TABLE 13

| Sample | Potency Unfiltered (mg/mL) | Potency 0.2 μm filtered (mg/mL) | Potency Retained (%) |
| --- | --- | --- | --- |
| Example 25 | 4.3 | 4.2 | 98 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A pharmaceutical composition comprising nanoparticles, said nanoparticles comprising:
   (a) a poorly water soluble drug having a solubility in water of less than 5 mg/mL over the pH range of 6.5 to 7.5 at 25° C., at least 90 wt % of said drug in said nanoparticles being non-crystalline;
   (b) ethylcellulose; and
   (c) a bile salt;
   wherein (i) said nanoparticles have an average size of less than 500 nm; (ii) said drug constitutes from 0.1 wt % to 75 wt %, said ethylcellulose constitutes from 2 wt % to 85 wt %, and said bile salt constitutes from 0.5 wt % to 60 wt % of the total mass of said drug, said ethylcellulose, and said bile salt in said nanoparticles; and (iii) said drug, said ethylcellulose, and said bile salt collectively constitute at least 80 wt % of said nanoparticles.

2. The composition of claim 1 wherein said drug, said ethylcellulose, and said bile salt collectively constitute at least 90 wt % of said nanoparticles.

3. The composition of claim 1 wherein said nanoparticles consist essentially of said drug, said ethylcellulose, and said bile salt.

4. The composition of claim 1 wherein said nanoparticles have an average size of less than 300 nm.

5. The composition of claim 1 wherein said drug constitutes from 1 wt % to 60 wt %, said ethylcellulose constitutes from 5 wt % to 60 wt %, and said bile salt constitutes from 1 wt % to 50 wt % of the total mass of said drug, said ethylcellulose, and said bile salt in said nanoparticles.

6. The composition of claim 1 wherein said bile salt is selected from the group consisting of taurocholate and salts thereof, glycocholate and salts thereof, and mixtures thereof.

7. The composition of claim 1 wherein said poorly water soluble drug is a hydrophobic non-ionizable drug having a Log P value of at least 4.0, and a solubility in water of less than 100 pg/mL over the pH range of 6.5 to 7.5 at 25° C.

8. The composition of claim 1 wherein said drug in said nanoparticles is present as a solid solution of said drug homogeneously distributed throughout at least one of said ethylcellulose and said bile salt.

9. A pharmaceutical composition comprising an aqueous suspension of the nanoparticles of claim 1.

10. The pharmaceutical composition of claim 9 further comprising a matrix material.

11. A process for forming nanoparticles comprising: (a) forming an organic solution comprising a poorly water soluble drug and ethylcellulose dissolved in a solvent, wherein said drug has a solubility in water of less than 5 mg/ml over the pH range of 6.5 to 7.5; (b) forming an aqueous solution comprising a bile salt, wherein said drug and said ethylcellulose are poorly soluble in said aqueous solution; (c) mixing said organic solution with said aqueous solution to form a first mixture; (d) removing said solvent from said first mixture to form a suspension comprising said nanoparticles and said aqueous solution, wherein (i) said nanoparticles have an average size of less than 500 nm; (ii) at least 90 wt % of said drug in said nanoparticles is non-crystalline; (iii) said drug constitutes from 0.1 wt % to 75 wt %, said ethylcellulose constitutes from 2 wt % to 85 wt %, and said bile salt constitutes from 0.5 wt % to 60 wt % of the total mass of said drug, said ethylcellulose, and said bile salt in said nanoparticles, and (iv) said drug, said ethylcellulose, and said bile salt collectively constitute at least 80 wt % of said nanoparticles.

12. The process of claim 11 wherein said organic solvent is selected from the group consisting of methylene chloride, ethyl acetate, cyclohexane and benzyl alcohol.

13. The process of claim 11 wherein said aqueous solution consists essentially of water and said bile salt.

14. A pharmaceutical composition comprising nanoparticles, said nanoparticles consisting essentially of:
(a) a poorly water soluble drug having a solubility in water of less than 5 mg/mL over the pH range of 6.5 to 7.5 at 25° C., at least 90 wt % of said drug in said nanoparticles being non-crystalline;
(b) ethylcellulose; and
(c) a bile salt;
wherein (i) said nanoparticles have an average size of less than 500 nm; (ii) said drug constitutes from 0.1 wt % to 75 wt %, said ethylcellulose constitutes from 2 wt % to 85 wt %, and said bile salt constitutes from 0.5 wt % to 60 wt % of the total mass of said drug, said ethylcellulose, and said bile salt in said nanoparticles; and (iii) said drug, said ethylcellulose, and said bile salt collectively constitute at least 80 wt % of said nanoparticles.

15. The composition of claim 1 in the form of a solid composition.

16. The composition of claim 15 further comprising a matrix material.

17. The composition of claim 14 in the form of a solid composition.

18. The composition of claim 17 further comprising a matrix material.

19. The composition of claim 16 or 18 wherein said matrix material is selected from the group consisting of polyvinyl pyrrolidone, trehalose, hydroxypropyl methyl cellulose, hydroxypropyl cellulose, casein, caseinate, albumin, gelatin, acacia, lactose, mannitol, and the pharmaceutically acceptable forms thereof.

* * * * *